US009909146B2

(12) United States Patent
Marliere

(10) Patent No.: US 9,909,146 B2
(45) Date of Patent: Mar. 6, 2018

(54) PRODUCTION OF ALKENES BY ENZYMATIC DECARBOXYLATION OF 3-HYDROXYALKANOIC ACIDS

(75) Inventor: Philippe Marliere, Sceaux (FR)

(73) Assignee: Scientist of Fortune S.A., Luxembourg (LU)

( * ) Notice: Subject to any disclaimer, the term of this patent is extended or adjusted under 35 U.S.C. 154(b) by 401 days.

(21) Appl. No.: 13/002,504

(22) PCT Filed: Jul. 6, 2009

(86) PCT No.: PCT/FR2009/051332
§ 371 (c)(1),
(2), (4) Date: Mar. 9, 2011

(87) PCT Pub. No.: WO2010/001078
PCT Pub. Date: Jan. 7, 2010

(65) Prior Publication Data
US 2011/0165644 A1    Jul. 7, 2011

Related U.S. Application Data

(60) Provisional application No. 61/078,824, filed on Jul. 8, 2008.

(30) Foreign Application Priority Data

Jul. 4, 2008 (FR) .................... 08 54550

(51) Int. Cl.
*C12P 5/02* (2006.01)
*C12N 9/88* (2006.01)
*C07C 2/28* (2006.01)

(52) U.S. Cl.
CPC ............... *C12P 5/026* (2013.01); *C07C 2/28* (2013.01); *C12N 9/88* (2013.01); *C12Y 401/01033* (2013.01)

(58) Field of Classification Search
CPC .......... C12P 5/026; C12N 9/88; C12N 9/001; C12Y 401/01033; C12Y 402/03027
USPC ................ 435/167, 232, 243, 189, 196, 135
See application file for complete search history.

(56) References Cited

FOREIGN PATENT DOCUMENTS

| CN | 101044243 A | 9/2007 |
|---|---|---|
| EP | 0 178 153 A2 | 8/1985 |
| EP | 0 205 303 A2 | 3/1986 |
| WO | WO 02/099095 A2 | 12/2002 |
| WO | WO-2006/018211 A1 | 2/2006 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Gogerty et al, Appld & Env Micriobiol 2010, pp. 8004-8010.*
Fujii et al., Appl. Microbiol. Biotechnol., 1987, vol. 25: 430-433.*
Office Action dated Dec. 25, 2012, issued in corresponding Chinese Application No. 200980125840.8.
Stinson, Robert A. et al., "β-Alanine as an ethylene precursor. Investigations towards preparation, and properties, of a soluble enzyme system from a subcellular particulate fraction of bean cotyledons," Plant Physiol., 1969, vol. 44, pp. 1217-1226.
Qiu, Yongge et al., "Progress in mevalonate 5-diphosate decarboxylase and its inhibition," Journal of Hanshan Normal University, Dec. 2007, vol. 28, No. 6, pp. 73-82.
GenBank Database, Accession No. YP_024134, diphosphomevalonate decarboxylase, Futterer O. et al., Dec. 3, 2007.
Lou, Jian et al. "Research and development of 3-hydroxypropionic acid by microbes and engineered cells," Industrial Microbiology, Dec. 31, 2006, vol. 36, Nol. 4, pp. 56-60.
Meier, Ingrid K. et al., Olefin Synthesis by Vanadium (V)-induced Oxidative Decarboxylation-Deoxygenation of 3-Hydroxy Carboxylic Acids, Journal of Organic Chemistry, 1990, 55, pp. 5619-5642.
Stinson, Robert A. et al., β-Alanine as an Ethylene Precursor. Investigations Towards Preparation, and Properties, of a Soluble Enzyme System From a Subcellular Particulate Fraction of Bean Cotyledons, Plant Physiology, (1969) 44, pp. 1217-1226.
English Translation of the Office Action dated Jul. 3, 2013, issued for RU Patent Application No. 2011 103 650; Scientist of Fortune S.A., Applicant.
Witkowski et al, "Conversion of a B-Ketoacyl Synthase to a Malonyl Decarboxylase by Replacement of the Active-Site Cysteine with Glutamine," American Chemical Society, Biochemistry, 1999, vol. 38, No. 36, pp. 11643-11650.
Chinese Office Action, dated Jun. 28, 2013, for Chinese Application No. 200980125840.8 with English language translation.
Database Accession No. Q6KZB1_PICTO—XP002579929.
Database Biosis—Accession No. PREV197764059311—XP002579930.
Database Biosis—Accession No. PREV200000216573—XP002579931.
English language translation of Russian Office Action, dated Feb. 21, 2014, for Russian Application No. 2011 103 650.
European Office Action, dated May 14, 2014, for European Application No. 09772760.6.
Jabalquinto et al., "Substrate binding order in mevalonate 5-diphosphate decarboxylase from chicken liver," Biochmica Et Biophysica Acta—Protein Structure and Molecular Enzymology, vol. 996, No. 3, Jul. 6, 1989, pp. 257-259.
Ladygina et al., "A review on microbial synthesis of hydrocarbons", Process Chemistry, vol. 41, No. 5, May 1, 2006, pp. 1001-1014 (XP027984109).
Toth et al., "Molecular cloning and expression of the cDNAs encoding human and yeast mevalonate pyrophosphate decarboxylase," J. of Bio. Chem., vol. 271, No. 14, Apr. 5, 1996, pp. 7895-7898.

* cited by examiner

*Primary Examiner* — Robert B Mondesi
*Assistant Examiner* — Mohammad Y Meah
(74) *Attorney, Agent, or Firm* — Michele M. Wales; InHouse Patent Counsel, LLC

(57) ABSTRACT

The present invention relates to a method for generating alkenes biologically. It relates more particularly to a method for producing terminal alkenes by enzymatic decarboxylation of 3-hydroxyalkanoate molecules. The invention also relates to the enzymatic systems and the microbial strains used, and also to the products obtained.

34 Claims, 11 Drawing Sheets

Figure 1:
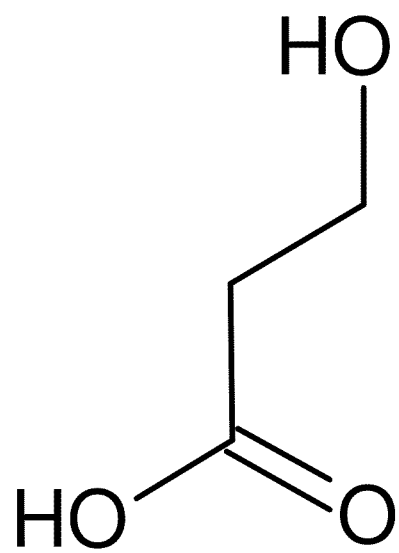

Reaction mechanism of mevalonate diphosphate decarboxylase EC 4.1.1.33

Fig. 2A Physiologic activity

Fig. 2B Generic activity 3-hydroxy-butyrate 3-hydroxy-3-methyl-butyrate 3-hydroxy-3-methyl-valerate Figure 4
Fig. 4A
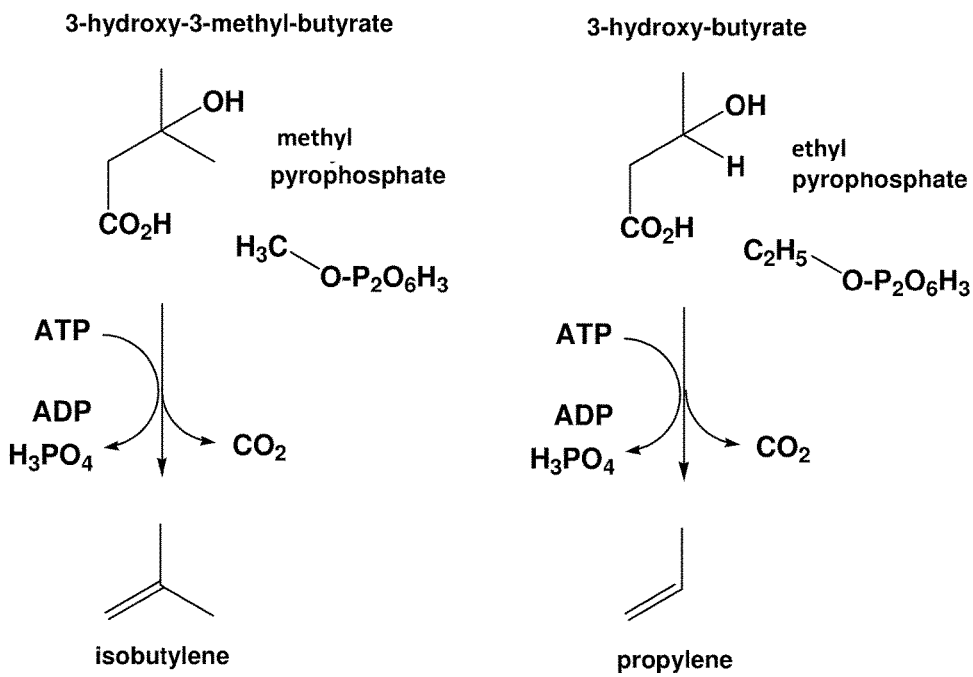
Fig. 4B
Fig. 4C
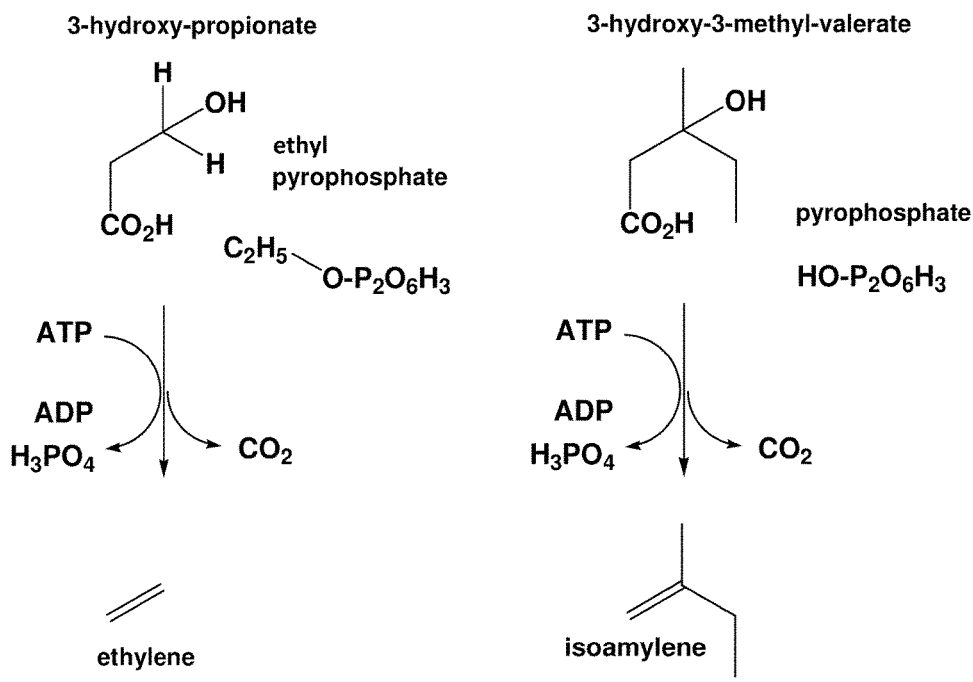
Fig. 4D Propionyl diphosphate Ethyl diphosphate Methyl diphosphate Pyrophosphate

PRODUCTION OF ALKENES BY ENZYMATIC DECARBOXYLATION OF 3-HYDROXYALKANOIC ACIDS

This Application is the National Phase Under 35 U.S.C. § 371 of PCT International Application No. PCT/FR2009/051332 which has an International filing date of Jul. 6, 2009, which claims priority to both U.S. Provisional Application No. 61/078,824 filed on Jul. 8, 2008 and to French Patent Application FR 08 54550 filed on Jul. 4, 2008. The entire contents of all applications listed above are hereby incorporated by reference.

INTRODUCTION

The present invention relates to a method for generating alkenes through a biological process. More specifically, the invention relates to a method for producing terminal alkenes (in particular propylene, ethylene, 1-butylene, isobutylene or isoamylene) from molecules of the 3-hydroxyalkanoate type.

BACKGROUND OF THE INVENTION

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Ethylene, the simplest alkene, lies at the heart of industrial organic chemistry: it is the most widely produced organic compound in the world. It is used in particular to produce polyethylene, a major plastic. Ethylene can also be converted to many industrially useful products by reaction (of oxidation, of halogenation).

Propylene holds a similarly important role: its polymerization results in a plastic material, polypropylene. The technical properties of this product in terms of resistance, density, solidity, deformability, and transparency are unequalled. The worldwide market for polypropylene has grown continuously since its invention in 1954.

Butylene exists in four forms, one of which, isobutylene, enters into the composition of methyl-tert-butyl-ether (MTBE), an anti-knock additive for automobile fuel. Isobutylene can also be used to produce isooctene, which in turn can be reduced to isooctane (2,2,4-trimethylpentane); the very high combustion/explosion ratio of isooctane makes it the best fuel for so-called "gasoline" engines. Amylene, hexene and heptene exist in many forms according to the position and configuration of the double bond. These products have real industrial applications but are less important than ethylene, propylene or butenes.

All these alkenes are currently produced by catalytic cracking of petroleum products (or by a derivative of the Fisher-Tropsch process in the case of hexene, from coal or gas). Their cost is therefore naturally indexed to the price of oil. Moreover, catalytic cracking is sometimes associated with considerable technical difficulties which increase process complexity and production costs.

Independently of the above considerations, the bioproduction of plastics ("bioplastics") is a thriving field. This boom is driven by economic concerns linked to the price of oil, and by environmental considerations that are both global (carbon-neutral products) and local (waste management).

The main family of bioplastics is that of the polyhydroxyalkanoates (PHA). These are polymers obtained by condensation of molecules comprising both an acid group and an alcohol group. Condensation takes place by esterification of the acid on the alcohol of the following monomer. This ester bond is not as stable as the direct carbon-carbon bond present in the polymers of conventional plastics, which explains why PHAs have a biodegradability of a few weeks to a few months.

The PHA family includes in particular poly-3-hydroxybutyrate (PHB), a polymer of 3-hydroxybutyrate, and poly-hydroxybutyrate-valerate (PHBV), an alternating polymer of 3-hydroxybutyrate and 3-hydroxyvalerate.

PHB is naturally produced by some strains of bacteria such as *Alcaligenes eutrophus* and *Bacillus megaterium*. Laboratory bacteria, like *E. coli*, having integrated synthetic pathways leading to PHB or to PHAs in general, have been constructed. The compound or its polymer can, in certain laboratory conditions, account for up to 80% of the bacterial mass (Wong M S et al., Biotech. Bioeng., 2008). Industrial-scale production of PHB was attempted in the 1980s, but the costs of producing the compound by fermentation were considered too high at the time. Projects involving the direct production of these compounds in genetically modified plants (having integrated the key enzymes of the PHB synthetic pathway present in producer bacteria) are in progress and might entail lower operating costs.

The production by a biological pathway of alkanes or other organic molecules that can be used as fuels or as precursors of synthetic resins is called for in the context of a sustainable industrial operation in harmony with geo-chemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Lady-gina N et al., Process Biochemistry, 2006, 41:1001; and Wackett LP, Current Opinions in Chemical Biology, 2008, 21:187.

In the alkene chemical family, isoprene (2-methyl-1,3-butadiene) is the terpene motif which, through polymerization, leads to rubber. Other terpenes might be developed, by chemical, biological or mixed pathway, as usable products such as biofuels or to manufacture plastics. The recent literature shows that the mevalonate pathway (a key intermediate in steroid biosynthesis in many organisms) might be used in order to efficiently produce products from the terpene family at industrial yields (Withers S T et al., Appl. Environ. Microbiol., 2007, 73:6277).

The production of terminal alkenes [ethylene mono- or di-substituted at position 2: $H_2C=C(R^1)(R^2)$] has apparently been less extensively investigated. The production of isobutylene from isovalerate by the yeast *Rhodotorula minuta* has been detected (Fujii T. et al., Appl. Environ. Microbiol., 1988, 54:583), but the efficiency of this conversion, less than 1 millionth per minute, or about 1 for 1000 per day, is far from permitting an industrial application. The reaction mechanism was elucidated by Fukuda H. et al. (BBRC, 1994, 201(2):516) and involves a cytochrome P450 enzyme which decarboxylates isovalerate by reduction of an oxoferryl group $Fe^V=O$. At no point does the reaction involve hydroxylation of isovalerate. Isovalerate is also an intermediate in leucine catabolism. Large-scale biosynthesis of isobutylene by this pathway seems highly unfavorable, since it would require the synthesis and degradation of one molecule of leucine to form one molecule of isobutylene.

Also, the enzyme catalyzing the reaction uses heme as cofactor, poorly lending itself to recombinant expression in bacteria and to improvement of enzyme parameters. For all these reasons, it appears very unlikely that this pathway of the prior art can serve as a basis for industrial exploitation. Other microorganisms have been described as being marginally capable of naturally producing isobutylene from isovalerate; the yields obtained are even lower than those obtained with *Rhodotorula minuta* (Fukuda H. et al, Agric. Biol. Chem., 1984, 48:1679).

These same studies have also described the natural production of propylene: many microorganisms are capable of producing propylene, once again with an extremely low yield.

The production of ethylene by plants has long been known (Meigh et al, 1960, Nature, 186:902). According to the metabolic pathway elucidated, methionine is the precursor of ethylene (Adams and Yang, PNAS, 1979, 76:170). Conversion of 2-oxoglutarate has also been described (Ladygina N. et al., Process Biochemistry 2006, 41:1001). Since a single ethylene molecule requires the previous production of a four- or five-carbon chain, the equipment and energy needs of all these pathways are unfavorable and do not bode well for their industrial application for alkene bioproduction.

Prior to the characterization of the enzymatic steps which, in plants, convert to ethylene its true metabolic precursor, S-adenosylmethionine (SAM) via formation of 1-aminocyclopropane-1-carboxylate (ACC) (Adams and Yang, PNAS, 1979, 76:170), several other hypotheses had been proposed in the scientific literature to explain ethylene production, among which was the decarboxylation of acrylate ($H_2C=CH-CO_2H$) originating from the dehydration of 3-hydroxyproprionate. Several articles specifically speculated on the metabolic pathway which would convert 3-hydroxypropionate to ethylene, via acrylate, in order to interpret radiotracer studies of ethylene production in which $^{14}C$-labelled substrates were supplied to plant tissue preparations: beta-alanine-2-$^{14}C$ to bean cotyledon extracts (Stinson and Spencer, Plant Physiol., 1969, 44:1217; Thompson and Spencer, Nature, 1966, 210:5036), and propionate-2-$_{14}C$ to banana pulp homogenates (Shimokawa and Kasai, Agr. Biol. Chem., 1970, 34(11):1640). All these hypotheses of the involvement of 3-hydroxypropionate and acrylate in metabolic ethylene production, which did not lead to characterization of enzyme activities, vanished from the scientific literature once the role of methionine, SAM and ACC was discovered (Hanson and Kende, Plant Physiology, 1976, 57:528; Adams and Yang, PNAS, 1979, 76:170).

Therefore, to my knowledge, there is currently no efficient method for producing terminal alkenes such as ethylene, propylene, 1-butylene, isobutylene, 1-amylene or isoamylene by microbiological synthesis. Such method would make it possible to avoid the use of petroleum products, and to lower the costs of producing plastics and fuels. Finally, it could potentially have a considerable global environmental impact by allowing carbon to be stored in solid form.

SUMMARY OF THE INVENTION

The present invention describes a method for carrying out the synthesis of alkene compounds though a biological process.

The invention is based on the design of a novel synthetic pathway for terminal alkene compounds based on the conversion of 3-hydroxyalkanoates. The invention is also based on the demonstration that said conversion can be carried out biologically, by using an enzyme of the decarboxylase type or variants thereof. The invention can be implemented in vitro, in cell-free systems, or by using microorganisms. The invention also relates to the production of alkenes from a carbon source, and particularly a carbohydrate (in particular glucose), a polyol (in particular glycerol), a biodegradable polymer (in particular starch, cellulose, poly-3-hydroxyalkanoate); the carbon source being converted by a microorganism to a metabolic intermediate belonging to the 3-hydroxyalkanoate family, which is then converted to terminal alkene.

More specifically, it is an object of the invention to provide a method for producing a terminal alkene, characterized in that it comprises a step of converting a 3-hydroxyalkanoate in the presence of an enzyme having decarboxylase activity.

Another object of the invention is based on the use of 3-hydroxyalkanoate compounds, as precursor or substrate, for the production of terminal alkene compounds.

In particular embodiments of the invention:
  3-hydroxypropionate is converted to ethylene; or
  3-hydroxybutyrate is converted to propylene; or
  3-hydroxyvalerate is converted to 1-butylene; or
  3-hydroxy-3-methylbutyrate (or 3-hydroxyisovalerate) is converted to isobutylene; or
  3-hydroxy-3-methylvalerate is converted to isoamylene.

The invention further relates to the use of a decarboxylase enzyme, or a microorganism producing a decarboxylase, for producing terminal alkene compounds from 3-hydroxyalkanoates.

The invention also relates to a composition comprising a microorganism producing a decarboxylase, a suitable culture medium and a 3-hydroxyalkanoate compound, or a carbon source which can be converted by the microorganism to a 3-hydroxyalkanoate compound.

Another object of the invention relates to a biocatalyst comprising a decarboxylase enzyme, or a microorganism producing a decarboxylase which decarboxylates a 3-hydroxyalkanoate compound to a terminal alkene.

Another object of the invention relates to a terminal alkene compound obtained by a method such as described in the invention.

A further object of the invention is an isolated or purified enzyme having decarboxylase activity and comprising all or part of SEQ ID NO: 6 or an enzyme having at least 15% sequence homology thereto.

Another object of the invention relates to the use of an enzyme having decarboxylase activity and comprising all or part of SEQ ID NO: 6, or an enzyme having at least 15% sequence homology thereto, for producing a terminal alkene.

Another object of the invention relates to a method for producing an enzyme having decarboxylase activity and comprising all or part of SEQ ID NO: 6 or an enzyme having at least 15% sequence homology thereto, the method comprising culturing a microorganism comprising a recombinant nucleic acid coding for said sequence in conditions allowing the expression of said sequence.

Another object of the invention relates to a microorganism comprising a recombinant nucleic acid coding for an enzyme having decarboxylase activity and comprising all or part of SEQ ID NO: 6 or an enzyme having at least 15% sequence homology thereto.

Definitions

"3-hydroxyalkanoate", as used herein, denotes any molecule comprising 3-hydroxypropionate as common motif (FIG. 1), and optionally one or two alkyl substitutions on carbon 3. Said alkyl residues or groups can be linear or branched. As used herein, the terms "alkoyl" and "alkyl" have the same meaning and are interchangeable. Likewise, the terms "residue" and "group" have the same meaning and are interchangeable. Methyl, ethyl, propyl, isopropyl, butyl, isobutyl groups are examples of said alkyl groups. Carbon 3 becomes a chiral center if the two alkyl substitutions are different. The present definition encompasses the two chiral forms, even if one of the two forms, for example the R form, is the main form produced naturally. Examples of 3-hydroxyalkanoates are presented in FIG. 3. Optionally, alkyl substituents can be added on carbon 2, which then may also become chiral (if the two substituents are different). Equally, the configurations of the 3-hydroxyalkanoate substrates in the present invention encompass all the stereoisomers. In a preferred manner, the 3-hydroxyalkanoates correspond either to 3-hydroxypropionate or to variants or derivatives of 3-hydroxypropionate in which one of the two or the two hydrogen atoms carried on carbon 3 are substituted by a motif composed solely of carbon and hydrogen atoms, the number of carbon atoms of said substituents ranging from 1 to 5, preferably from 1 to 3, such as methyl, ethyl, propyl, isopropyl, butyl or isobutyl. The suffix "oate", as used herein, can interchangeably denote either the carboxylate ion (COO—) or carboxylic acid (COOH). It is not used to denote an ester. In a particular embodiment, the 3-hydroxyalkanoates are represented by the following formula: HO—CO—CH$_2$—C(R$^1$)(R$^2$)—OH or O$^-$—CO—CH$_2$—C(R$^1$)(R$^2$)—OH.

"Terminal alkenes", according to the present invention, denotes molecules composed solely of carbon and hydrogen (unsaturated hydrocarbons having the formula CnH2n) comprising ethylene and organic molecules derived from ethylene by mono- or di-substitution of the two hydrogen atoms bound to carbon 2 by linear or branched alkyl groups. Terminal alkenes preferably are represented by the formula H2C=C(R$^1$)(R$^2$) wherein R$^1$ and R$^2$ are selected, independently, in the group consisting of a hydrogen atom and a linear or branched alkyl group, preferably having 1 to 4 carbon atoms, more preferably from 1 to 3 carbon atoms. Preferably, at least one of the two substituents on carbon 2 of the alkene is a linear or branched alkyl group. Terminal alkenes comprise branched isoalkene compounds, such as for example isobutylene. Preferred examples of terminal alkene compounds according to the invention are in particular ethylene, propylene, isobutylene, and isoamylene (FIG. 4), or else 1-butylene and 1-amylene.

"Carbon source", as used herein, denotes any carbon compound that can be used as substrate for the organisms according to the invention. Said term includes glucose or any other hexose, xylose or any other pentose, polyols such as glycerol, sorbitol or mannitol, or else polymers such as starch, cellulose or hemicellulose, or else poly-3-hydroxyalkanoates like poly-3-hydroxybutyrate. It may be any substrate allowing the growth of microorganisms, such as formate for example. It may also be CO$_2$ in the case where the organisms are capable of carrying out photosynthesis.

"Recombinant", as used herein, denotes the artificial genetic modification of an organism, either by addition, removal, or modification of a chromosomal or extra-chromosomal gene or regulatory motif such as a promoter, or by fusion of organisms, or by addition of a vector of any type, for example plasmidic. The term "recombinant expression" denotes the production of a protein involving a genetic modification, preferably in order to produce a protein of exogenous or heterologous origin with respect to its host, that is, which does not naturally occur in the production host, or in order to produce a modified or mutated endogenous protein.

"Overexpression" or "overexpressing", as used herein, denotes the recombinant expression of a protein, preferably originating from an organism different from the one in which it is expressed, increased by at least 10% and preferably by 20%, 50%, 100%, 500% and possibly more as compared to the natural expression of said protein. This definition also encompasses the case where there is no natural expression of said protein.

A "co-substrate" is a product added to the enzymatic reaction, so as to improve certain parameters thereof, and above all the activity thereof, said product and the principal substrate being consumed in equal amounts. The co-substrate must therefore be added to the reaction at a concentration comparable to that of the principal substrate. Depending on the enzyme, the presence of a co-substrate may be required for the enzymatic reaction.

A "cofactor" is a product added to the enzymatic reaction, so as to improve certain parameters thereof and above all to improve the activity thereof, said product not being consumed during the reaction, and therefore needing only to be added at a low concentration, proportional to the amount of enzyme, said concentration therefore being referred to as "catalytic".

A "part" of an amino acid sequence denotes a fragment comprising at least 10, preferably at least 20, 30, 40 or 50 consecutive amino acid residues of said sequence.

"Homology" denotes the existence of a similarity between two sequences as measured by the percent identity between said two sequences.

Chemical compounds are often known by several names, official or common. Herein, the common names of the molecules are preferred. Thus:
  "ethylene" is used to denote ethene
  "propylene" is used to denote propene
  "butylene" is used to denote butene
  "isobutylene" is used to denote 2-methylpropene or isobutene
  "amylene" is used to denote pentene
  "isoamylene" is used to denote 2-methyl-but-1-ene or isopentene
  "propionate" is used to denote propanoic acid or the propanoate ion
  "butyrate" is used to denote butanoic acid or the butanoate ion
  "valerate" is used to denote pentanoic acid or the pentanoate ion.

DETAILED DESCRIPTION OF THE INVENTION

In particular, the invention provides a method for producing terminal alkenes comprising a step of enzymatic decarboxylation of 3-hydroxyalkanoate compounds. The invention also relates to the use of decarboxylases to catalyze this reaction, and in particular of enzymes of the type mevalonate diphosphate decarboxylase, and of substrates such as 3-hydroxybutyrate, 3-hydroxyvalerate, 3-hydroxy-3-methylbutyrate (or 3-hydroxyisovalerate) and 3-hydroxypropionate.

The invention describes the use of cofactors, including ethyl diphosphate, propyl diphosphate, methyl diphosphate, analogs of said molecules, and pyrophosphate. The invention further describes the use of co-substrates, such as ATP or other compounds containing a phosphoanhydride bond.

The invention also relates to the use of carbon sources, such as glucose, for directly producing terminal alkenes from whole cells, the synthetic pathway taking place by way of 3-hydroxyalkanoates.

The invention further relates to natural or modified organisms, endogenously producing a 3-hydroxyalkanoate, and also expressing a decarboxylase converting said 3-hydroxyalkanoates to terminal alkenes.

The alkene compounds produced, in particular propylene, ethylene and isobutylene, are key molecules in the plastics and fuel industry, and their industrial production by biological pathway, from renewable resources, represents a major innovation.

Figure 2:
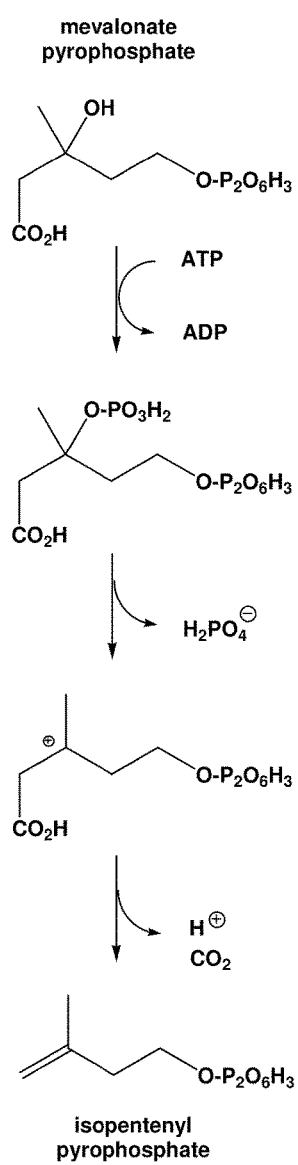
Figure 2:
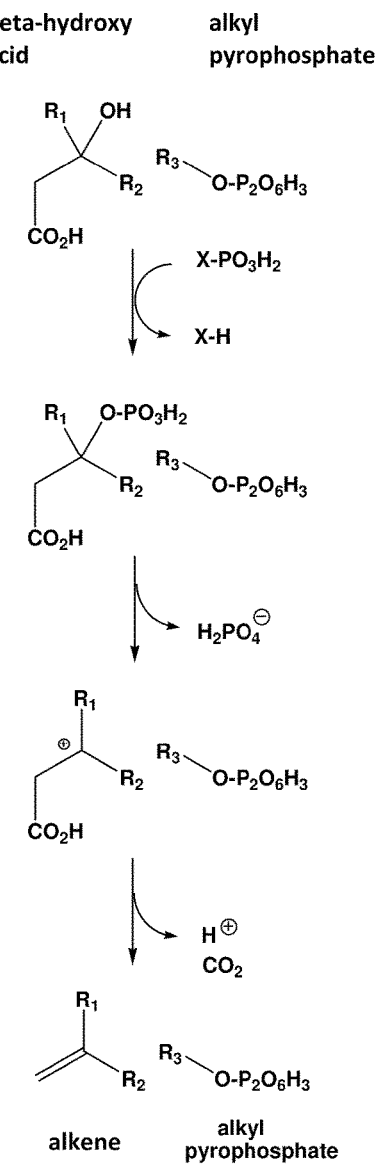

Thus the invention follows from the design of a novel synthetic pathway for compounds of the terminal alkene type based on the conversion of compounds of the 3-hydroxyalkanoate type. The invention demonstrates that said conversion can be carried out biologically, by using an enzyme of the decarboxylase type, which enables the conversion of a 3-hydroxyalkanoate to a terminal alkene. As illustrated in FIG. 2, said conversion takes place via a reaction intermediate having a 3-phospho-hydroxyalkanoate structure.

The conversion step according to the invention can be carried out in vitro, in the presence of an isolated enzyme (or an enzyme system additionally comprising one or more cofactors) or in culture, in the presence of a microorganism producing the enzyme.

As described herein in example 5, a signal-to-noise ratio (measured in the absence of enzyme) of approximately 100-fold for the conversion yield could be observed in some conditions. The affinity for 3-hydroxyisovalerate (HIV) was measured at approximately 40 mM. It was not obvious that such a very significant enzymatic activity could be obtained: indeed, biochemists familiar with the theory and practice of enzymology know very well that enzyme active sites contain structural elements enabling the recognition, binding and chemical conversion of certain specific substrates. The scientific literature abounds with experimental data indicating that changes in size or electrical charge, even minor, can lead to the exclusion of substrates. Specifically, no scientific prediction allowed it to be anticipated that MDP decarboxylases could use, as substrate, molecules of the 3-hydroxyalkanoate type in general, and 3-hydroxyisovalerate in particular, the latter differing from mevalonate diphosphate not only by its size (MW 118 versus 308 for mevalonate diphosphate), but also by the electrical charges of the diphosphate group present on the natural substrate, mevalonate diphosphate.

In a particular embodiment, a cofactor is added to the reaction so as to provide steric or electronic complementation in the catalytic cleft. The cofactor is advantageously selected in the group consisting of the pyrophosphate ion, methyl diphosphate, ethyl diphosphate, or propyl diphosphate. More generally, the cofactor is a compound containing the phosphoanhydride motif, having the general formula $R-O-PO_2H-O-PO_3H_2$ in which R represents in particular a hydrogen atom, a linear, branched or cyclic alkyl group, preferably having from 1 to 10 or from 1 to 5 carbon atoms, or any other monovalent organic group. The analagous motifs corresponding to the monoesters of methylene diphosphonate, represented by the general formula $R-O-PO_2H-CH_2-PO_3H_2$ in which phosphoanhydride is replaced by a methylene bridge having the advantage of not being hydrolyzed, are also part of the invention.

In a preferred embodiment, the conversion occurs in the presence of a co-substrate, said co-substrate preferably being a compound containing a phosphoanhydride, and preferably being ATP, an rNTP, a dNTP or a mixture of several of these molecules, a polyphosphate, or pyrophosphate. The co-substrate is generally present in the host. However, in another particular embodiment, a co-substrate can be added to the reaction, preferably selected in the group consisting of ATP, an rNTP, a dNTP, a mixture of several rNTPs or dNTPs, a polyphosphate, and preferably pyrophosphate, or a compound containing a phosphoanhydride (represented by the general formula $X-PO_3H_2$ of FIG. 2).

In a particular embodiment of the invention, a microorganism that produces the decarboxylase is used. In a preferred embodiment, the microorganism is recombinant in that it produces a heterologous decarboxylase relative to the production host. The method can thus be carried out directly in the culture medium, without the need to separate or purify the enzyme system. In an especially advantageous manner, a microorganism is used having the natural or artificial property of endogenously producing one or more 3-hydroxyalkanoates, and also expressing or overexpressing a decarboxylase, natural or modified, so as to produce terminal alkenes directly from a carbon source present in solution.

The microorganisms used in the invention can be prokaryotes or eukaryotes, and in particular bacteria, yeasts, plant cells, fungi and molds, animal cells. In a particular embodiment, the microorganisms are bacteria, in particular the strain *Alcaligenes eutrophus* or *Bacillus megaterium*.

In another particular embodiment, the microorganisms are recombinant bacteria of an *Escherichia coli* strain having been modified so as to endogenously produce one or more 3-hydroxyalkanoates, and converting them to terminal alkenes.

In another particular embodiment the microorganisms are recombinant yeasts, producing 3-hydroxyalkanoates, and converting them to terminal alkenes.

In another particular embodiment, one uses a microorganism that produces one or more 3-hydroxyalkanoates on the one hand, and a decarboxylase, optionally expressed by a second microorganism, on the other hand. Optionally, one cultures and one concomitantly uses the two organisms in the method according to the invention.

In another particular embodiment, whole plants or animals, optionally modified by transgenesis, are used to produce terminal alkenes from 3-hydroxyalkanoates, whether these be produced endogenously or exogenously supplied.

In another particular embodiment, one uses a photosynthetic microorganism having the natural or artificial property of endogenously producing one or more 3-hydroxyalkanoates, and also overexpressing a decarboxylase, natural or modified, so as to produce terminal alkenes directly from $CO_2$ present in solution. Preferably, the microorganism is a photosynthetic bacterium, or a microalgae.

The present invention further relates to the organisms described hereinabove and their use for producing terminal alkene compounds.

As described in the following, the method of the invention can be carried out in microaerophilic conditions.

Furthermore, in a preferred embodiment, the method is carried out in the presence of a system for collecting gas of terminal alkenes degassing from the reaction.

Decarboxylase, as used herein, denotes any enzyme able to convert a 3-hydroxyalkanoate with a number n of carbon atoms to a terminal alkene compound with a number n−1 of carbon atoms. As illustrated in FIG. 2, the inventive method preferably takes place via a 3-phospho-hydroxyalkanoate reaction intermediate, and the enzyme used advantageously possesses a decarboxylase activity and a phosphorylase activity.

In a particular embodiment, the decarboxylase is a member of the phylogenetic superfamily of mevalonate diphosphate (MDP) decarboxylase (enzyme nomenclature EC 4.1.1.33), that is to say, a natural or artificial enzyme, encoded by a native or synthetic gene, optionally able to catalyze the reaction illustrated in FIG. 2.

MDP decarboxylase is an enzyme involved in cholesterol biosynthesis. Said enzyme has been isolated from a variety of organisms including animals, fungi, yeasts and some bacteria. It can also be expressed by some plants (Lalitha et al., 1985). Many genes encoding this enzyme have been cloned and sequenced. These enzymes are generally composed of 300 to 400 amino acids and use ATP as co-substrate, which is converted during the reaction to ADP and inorganic phosphate. The phosphate group is transferred from the ATP molecule to the tertiary alcohol of mevalonate diphosphate, releasing ADP. The reaction intermediate phosphorylated on the 3-hydroxyl group then undergoes elimination of the phosphate group, in the physiological case releasing isopentenyl pyrophosphate (FIG. 2).

The three-dimensional structures of several enzymes from this family have been resolved. To date, relatively few studies have been carried out on the enzymes from this family, and these enzymes have only been investigated in the context of precisely describing the cholesterol biosynthetic pathway. On the other hand, to my knowledge, no studies have yet been done to divert this enzyme from its natural function and turn it into an industrial catalyst.

Several examples of MDP decarboxylases from different organisms are given in sequences SEQ ID NO: 1 to SEQ ID NO: 16.

Thus, in a preferred embodiment, the enzyme used is a decarboxylase, preferably comprising an amino acid sequence selected from the group consisting of SEQ ID NO: 1, 2, 3, 4, 5, 6, 7, 8, 9, 10, 11, 12, 13, 14, 15 or 16 or a sequence possessing at least 15% sequence homology to one of said sequences and retaining a decarboxylase activity. Preferred enzymes advantageously have at least 50% sequence homology, preferably at least 80%, more preferably at least 85%, even more preferably, at least 90, 95, 96, 97, 98 or 99% homology to one of the primary sequences SEQ ID NO: 1, 2, 3, 4, 5, 6, 7, 8, 9, 10, 11, 12, 13, 14, 15 and 16. The percent of sequence homology can be determined by different methods and by means of software programs known to one of skill in the art, such as for example the CLUSTAL method or BLAST and derived software, or by using a sequence comparison algorithm such as that described by Needleman and Wunsch (J. Mol. Biol., 1970, 48:443) or Smith and Waterman (J. Mol. Biol., 1981, 147:195).

A preferred decarboxylase of the invention is represented by the enzyme having sequence SEQ ID NO: 6, as well as any enzyme having significant sequence homology thereto. Preferred enzymes advantageously have at least 50% sequence homology, preferably at least 80%, more preferably at least 85%, even more preferably at least 90, 95, 96, 97, 98 or 99% sequence homology to the primary sequence SEQ ID NO: 6. Said enzyme has been cloned from *Picrophilus torridus* and produced by recombinant means in the scope of the present invention. As illustrated in the examples, this enzyme is particularly efficient at producing terminal alkene compounds according to the present invention. This enzyme is also an object of the present invention, as are the preparation and the use thereof as catalyst. In particular, an object of the invention is the use of a decarboxylase enzyme comprising all or part of SEQ ID NO: 6 or an enzyme having a significant sequence homology and preferably at least 15% to SEQ ID NO: 6, for producing terminal alkene compounds. Significant sequence homology denotes a sequence homology detectable by using the aforementioned algorithms, and preferably a sequence homology greater than 15%. The organisms with the closest phylogenetic relationship to *Picrophilus torridus*, such as *Ferroplasma acidarmanus*, *Thermoplasma acidophilum*, *Thermoplasma volcanium* and *Picrophilus oshimae*, are able to produce MDP decarboxylases closest to that of SEQ ID NO: 6. For instance, the MDP decarboxylase of *Thermoplasma acidophilum* (AC number Q9HIN1) has 38% sequence homology to SEQ ID NO: 6; that of *Thermoplasma volcanium* (Q97BY2) has approximately 42%. The use of these MDP decarboxylases is more particularly considered in the present invention.

Other enzymes of the decarboxylase type, natural or synthetic, can be selected for their ability to produce terminal alkenes according to the invention. Thus, a selection test comprises contacting the purified enzyme, or a microorganism producing the enzyme, with the substrate of the reaction and measuring the production of the terminal alkene compound. Such tests are described in the experimental section, in which over 60 different enzymes were tested.

The enzyme that is used can be any decarboxylase that is natural or produced or artificially optimized. In particular, one advantageously uses a decarboxylase having an optimized activity with respect to one or more 3-hydroxyalkanoates.

The enzyme can be produced or selected, from a reference decarboxylase (natural or itself already synthetic or optimized), by protein engineering techniques such as random mutagenesis, massive mutagenesis, site-directed mutagenesis, DNA shuffling, synthetic shuffling, in vivo evolution, or complete synthesis of genes.

In this respect, one object of the invention also relates to a method for preparing an enzyme having decarboxylase activity towards a 3-hydroxyalkanoate substrate, the method comprising a step of treating an enzyme source and selecting an enzyme having enhanced properties towards said substrate, as compared to the untreated enzyme.

The enzyme used in the invention can thus be natural or synthetic, and produced by chemical, biological or genetic means. It can also be chemically modified, for example in order to improve its activity, resistance, specificity, purification, or to immobilize it on a support.

The invention is characterized by the use of a decarboxylase, in particular a natural or modified MDP decarboxylase, to convert 3-hydroxyalkanoates to terminal alkenes.

The natural substrate of MDP decarboxylase is mevalonate diphosphate, which does not fall under the definition of 3-hydroxyalkanoates.

The generic reaction carried out by MDP decarboxylase using various 3-hydroxyalkanoates is depicted in FIG. 2B. It is understood that these reactions lead directly and in a single step to terminal alkenes.

In a first embodiment, the native or recombinant enzyme, purified or not, is used to convert a 3-hydroxyalkanoate to terminal alkene. To do this, the enzyme preparation is incubated in the presence of the substrate in physicochemical conditions allowing the enzyme to be active, and the incubation is allowed to proceed for a sufficient period of time. At the end of the incubation, one optionally measures the presence of the terminal alkene by using any detection system known to one of skill in the art such as gas chromatography or colorimetric tests for measuring the formation of the alkene product, or of free phosphate, or else for measuring the disappearance of the 3-hydroxyalkanoate substrate or of ATP.

Figure 5:
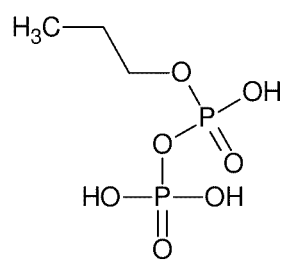
Figure 5:
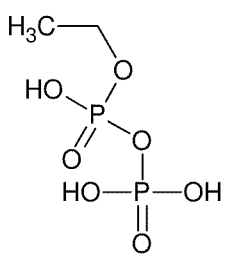
Figure 5:
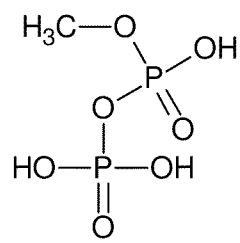
Figure 5:
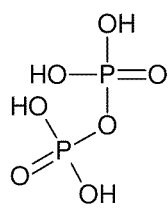

In a preferred embodiment, cofactors are added so as to best mimic the natural reaction. In fact, the structure of 3-hydroxyalkanoates generally corresponds to a fragment of MDP, thus leaving a large space in the catalytic cleft empty during enzyme-substrate binding. Filling this space with a cofactor to replace the missing part of the substrate has the purpose of most closely mimicking the MDP molecule. As the cofactor is not modified during the reaction, it will therefore be added only in catalytic amounts. In the case where the substrate of the reaction is 3-hydroxypropionate, the complementary cofactor will be propyl diphosphate. In the case where the substrate is 3-hydroxybutyrate or 3-hydroxy-3-methylbutyrate, the complementary cofactor will be ethyl diphosphate. In the case where the substrate is 3-hydroxyvalerate or 3-hydroxy-3-methylvalerate, the complementary cofactor will be methyl diphosphate. These different molecules are shown in FIG. 5. By chance, it may happen that the complementary cofactor of a reaction has a positive effect on the reaction of another substrate. Generally, the cofactor can be any molecule comprising a phosphoanhydride, and therefore having the general formula $R-PO_2H-O-PO_3H_2$, in which R is in particular H, a linear, branched or cyclic alkyl group, or any other monovalent organic group. The analogous motifs corresponding to methylene diphosphonate monoesters, having the general formula $R-O-PO_2H-CH_2-PO_3H_2$ in which phosphoanhydride is replaced by a methylene bridge having the advantage of not being hydrolyzed, are also part of the invention.

More generally, the cofactors can be monophosphate, or even phosphate-free, analogs of the previous molecules, or else any other molecule that can improve the reaction yield by providing steric or electronic complementation in the enzyme catalytic site.

In a particular embodiment, a co-substrate is added to the reaction. Said cosubstrate can be either ATP, that is to say, the natural co-substrate of MDP decarboxylase, or any rNTP (ribonucleoside triphosphate) or dNTP (deoxyribonucleoside triphosphate) or any mixture of rNTP or dNTP, or else pyrophosphate, or another polyphosphate, or else any molecule containing a phosphoanhydride group ($X-PO_3H_2$ of FIG. 2).

In a preferred embodiment, for converting a 3-hydroxyalkanoate to terminal alkene one uses an enzyme having at least 15% sequence homology, preferably at least 30%, 50% and even more preferably at least 80, 90, 95, 96, 97, 98 or 99% to a natural enzyme having decarboxylase activity and in particular to one of the enzymes corresponding to sequences SEQ ID NO: 1 to 16. In particular, the enzyme can have been modified by engineering from one of the enzymes SEQ ID NO: 1 to 16, or from any other decarboxylase identified from other sources. Such enzyme may have lost its MDP decarboxylase activity in particular through genetic engineering in the laboratory, but also during natural evolution (in which case one can speak of vestige MDP decarboxylase) and retained or increased its activity towards one or more molecules of the 3-hydroxyalkanoate type. The generation of variants of these enzymes, more reactive towards said substrates, makes it possible to improve the yield of the reaction according to the invention. For instance, the reactivity of wild-type MDP decarboxylase towards 3-hydroxyalkanoates is not necessarily optimal. Any approach known to one of skill in the art by which to produce and select such variants, such as random mutagenesis, site-directed mutagenesis, massive mutagenesis, DNA shuffling, or in vivo evolution, can be used.

The invention is also characterized by the use of a totally artificial enzyme, obtained by designing and producing a synthetic gene coding for a totally new enzyme with the aim of converting a 3-hydroxyalkanoate to terminal alkene, by using or not using the known data on MDP decarboxylases to design it.

Another object of the invention is an isolated or purified enzyme having decarboxylase activity and comprising all or part of SEQ ID NO: 6.

Another object of the invention relates to the use of an enzyme having decarboxylase activity and comprising all or part of sequence SEQ ID NO: 6, or an enzyme having sequence homology such as described above, for producing a terminal alkene. In one variant, the sequence can further comprise additional residues, such as for example a Histidine tag at the N-terminal end.

Another object of the invention relates to a method for producing an enzyme having decarboxylase activity and comprising all or part of sequence SEQ ID NO: 6, or an enzyme having a sequence homology such as described above, the method comprising culturing a microorganism comprising a recombinant nucleic acid coding for said sequence in conditions allowing the expression of said sequence. In this context, the present invention describes, in addition to the native nucleic acid (SEQ ID NO: 19), a nucleic acid having a sequence that is optimized for expression of the enzyme SEQ ID NO: 6 in bacteria, in particular in *E. coli* (SEQ ID NO: 17). This nucleic acid, and any optimized nucleic acid (i.e. allowing at least 30% improvement in expression as compared to the wild type sequence), are an object of the present application.

Another object of the invention relates to a microorganism comprising a recombinant nucleic acid coding for an enzyme having decarboxylase activity and comprising all or part of SEQ ID NO: 6, or an enzyme having a sequence homology such as described above. The microorganism is preferably a bacterium, a yeast or a fungus. The invention also relates to any plant or non-human animal comprising a recombinant nucleic acid coding for a decarboxylase according to the invention.

In one embodiment, the MDP decarboxylase is used in purified form to convert 3-hydroxyalkanoates to terminal alkenes. However, this method is costly, since enzyme and substrate production and purification costs are high.

In another embodiment, the MDP decarboxylase is present in the reaction as a non-purified extract, or else in the form of non-lysed bacteria, so as to economize on protein purification costs. However, the costs associated with this method are still quite high due to the costs of producing and purifying the substrates.

In another embodiment of the invention, the method uses a living organism producing the enzyme by which to carry out the conversion. The invention is thus characterized by the genetically engineered modification of a bacterial strain producing one or more 3-hydroxyalkanoates [for example *Alcaligenes eutrophus* or *Bacillus megaterium*, or else an *E. coli* strain laboratory-modified to produce said product(s)], such that said bacterial strain overexpresses the decarboxylase, said enzyme preferably originating from an organism different from the host microorganism, and can directly generate one or more terminal alkenes. The genetic modification can consist in integrating a decarboxylase gene into the chromosome, expressing the enzyme on a plasmid containing a promoter upstream of the enzyme-coding sequence, the promoter and coding sequence preferably originating from different organisms, or any other method known to one of skill in the art. Alternatively, other bacteria or yeasts may have specific advantages and be chosen. For instance, a yeast such as *Saccharomyces cerevisiae*, an extremophilic bacteria such as *Thermus thermophilus*, or anaerobic bacteria from the family Clostridiae for example, microalgae, or photosynthetic bacteria can be used. So as to optimally produce the 3-hydroxyalkanoate(s), which will then be converted to terminal alkenes, the strains can also have been modified by genetic engineering, i.e., by in vitro recombination or by directed in vivo evolution.

In one embodiment, the inventive method is characterized by the conversion of a carbon source such as glucose, to 3-hydroxyalkanoate, followed by the conversion of said primary product into a secondary product, that is to say, terminal alkene. The different steps of said method are outlined in FIG. 6.

In a particular embodiment, the invention is characterized by the conversion of polyhydroxyalkanoates to 3-hydroxyalkanoate, by using an enzyme or a suitable physicochemical method, followed by the conversion of said primary product to secondary product, that is to say, terminal alkene. Optionally, the polyhydroxyalkanoate has been produced by a plant whose metabolic pathways have been modified in a way so that they produce high yields of polyhydroxyalkanoate.

In a particular embodiment, the invention consists in the integral method for producing products from atmospheric $CO_2$ or from $CO_2$ artificially added to the culture medium. The inventive method is implemented in an organism able to carry out photosynthesis, such as microalgae for example.

In these embodiments, the inventive method is further characterized by the mode of recovery of the products, which degas from the culture. As a matter of fact, short terminal alkenes, and particularly ethylene, propylene, butene isomers, adopt the gaseous state at room temperature and atmospheric pressure. The inventive method therefore does not require extraction of the product from the liquid culture medium, a step which is always very costly when performed on an industrial scale. The evacuation and storage of the gaseous hydrocarbons, and their possible subsequent physical separation and chemical conversion, can be performed according to any method known to one of skill in the art.

In a particular embodiment, the invention also comprises detecting the alkene (propylene, ethylene and isobutylene in particular) present in the gas phase of the method. The presence of the target compounds in an environment of air or another gas, even in small amounts, can be detected by using various techniques, and in particular by using gas chromatography systems with infrared or flame ionization detection, or by coupling with mass spectrometry.

In a particular embodiment, the terminal alkenes obtained are condensed, then optionally reduced, by using techniques known to one of skill in the art, so as to produce longer chain alkenes, or longer chain alkanes. In particular, isobutylene can be used to synthesize isooctane: the catalytic methods for successfully carrying out this reaction have already been described in detail.

In a particular embodiment, the method involves culturing microorganisms in standard culture conditions (30-37° C. at 1 atm, in a fermenter allowing aerobic growth of the bacteria) or non-standard conditions (higher temperature to correspond to the culture conditions of a thermophilic organism, for example).

In a particular embodiment, the microorganisms are cultured in microaerophilic conditions, the quantity of injected air being limiting so as to minimize residual oxygen concentrations in the gaseous effluents containing the alkene hydrocarbons.

Other aspects and advantages of the invention will be described in the following examples, which are given for the purpose of illustration and not by way of limitation.

LEGENDS OF DRAWINGS

Figure 3:
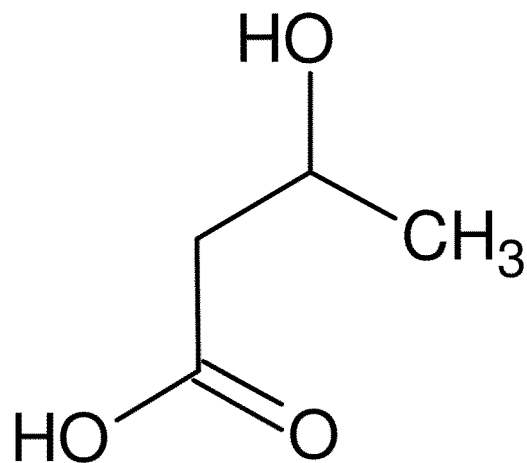
Figure 3:
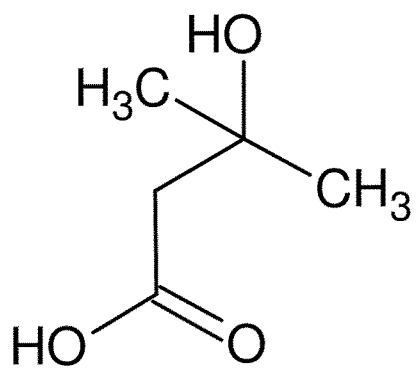
Figure 3:
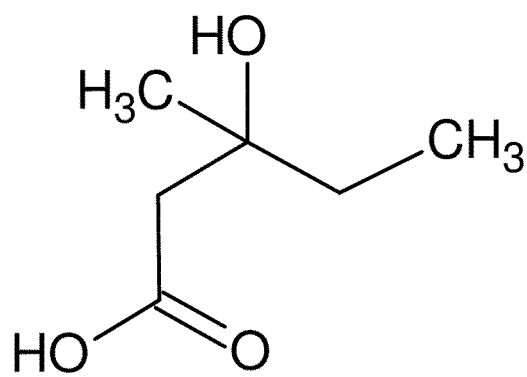
Figure 6:
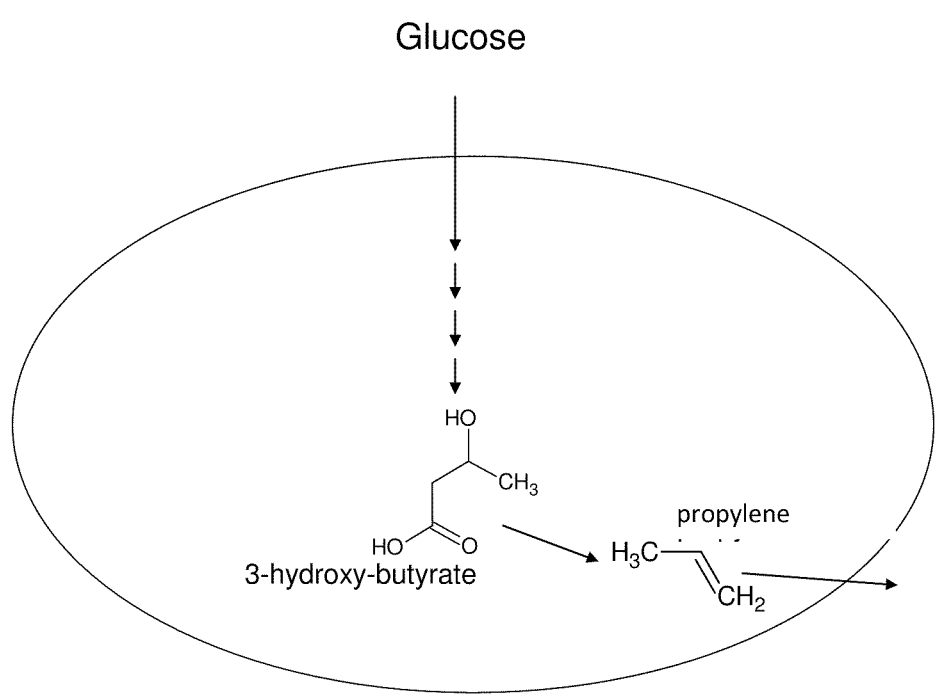
Figure 7:
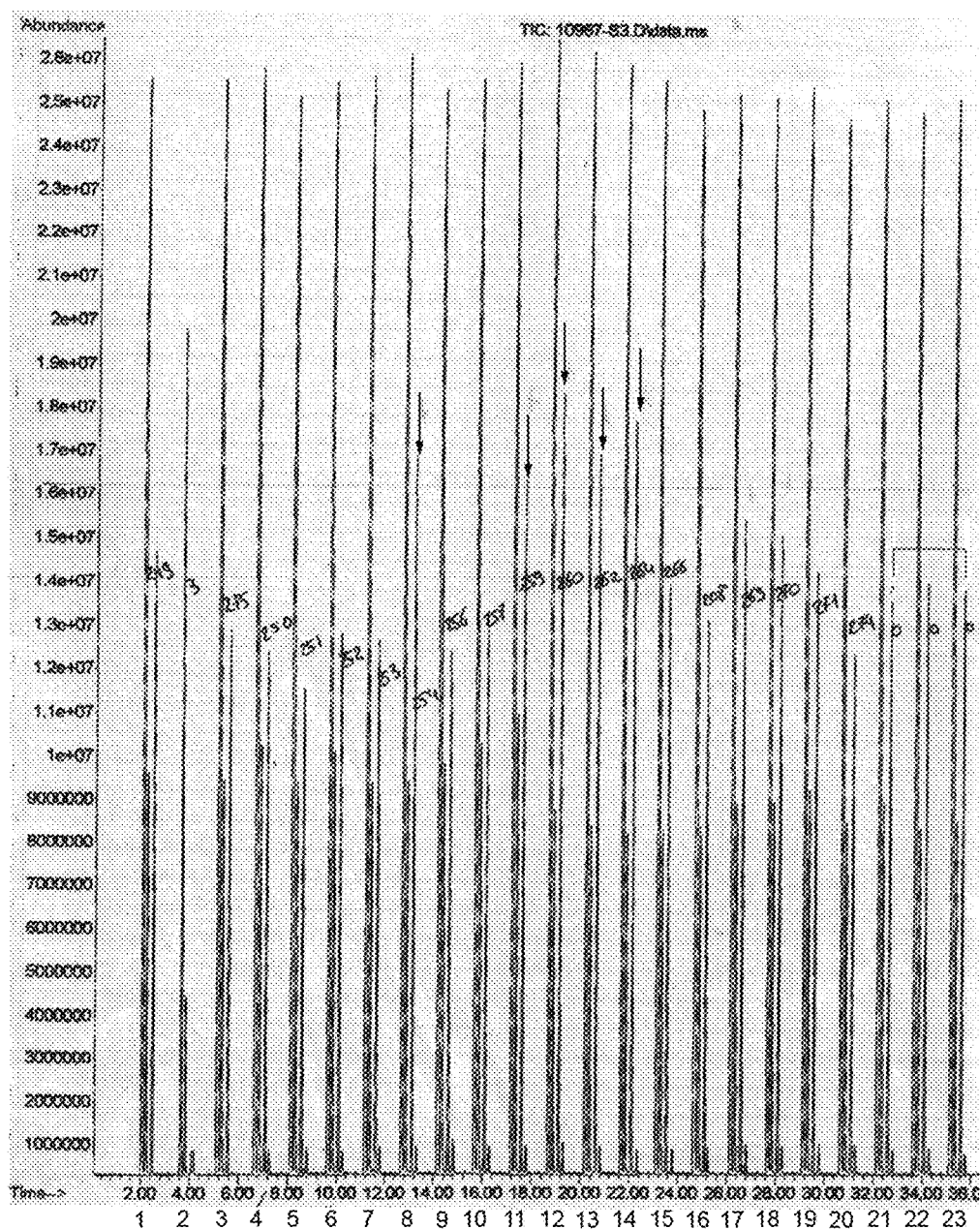
Figure 8:
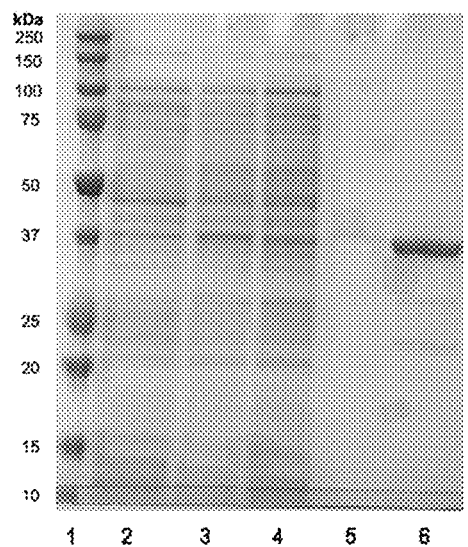
Figure 9:
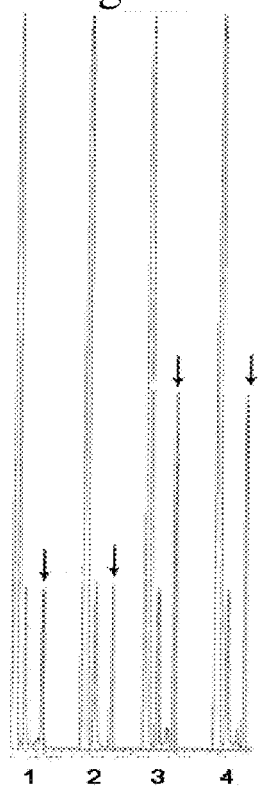
Figure 10:
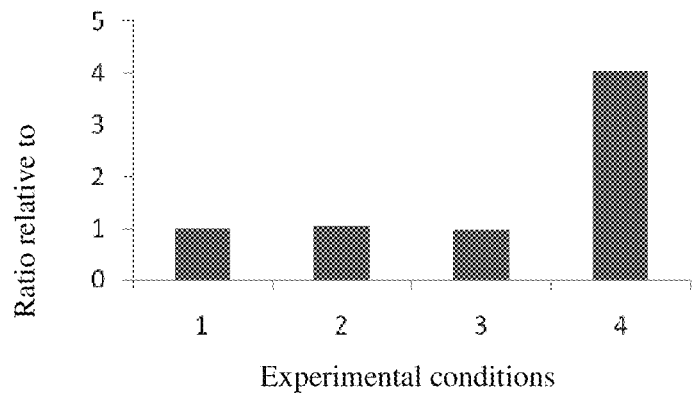
Figure 11:
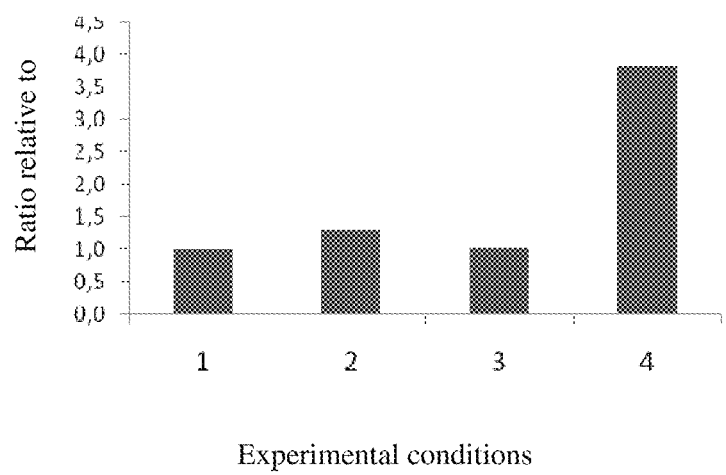
Figure 12:
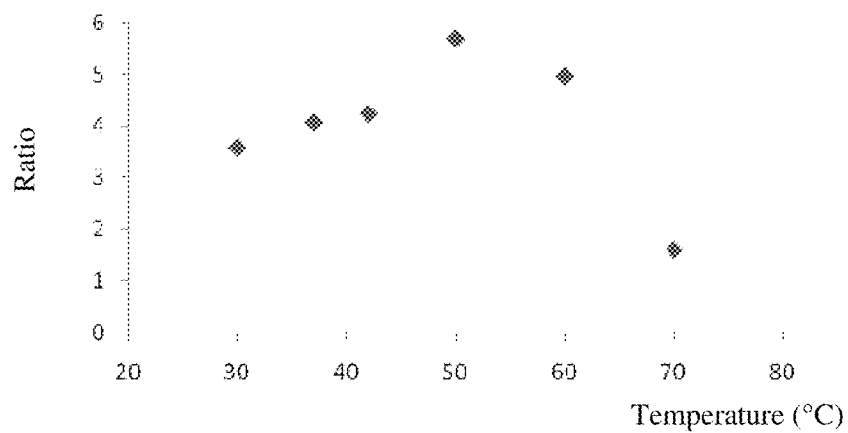
Figure 13:
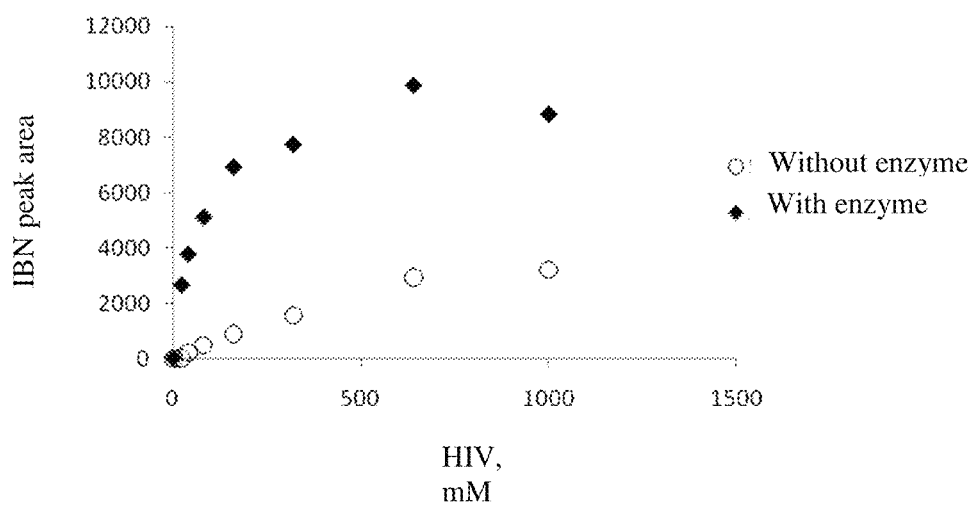
Figure 14:
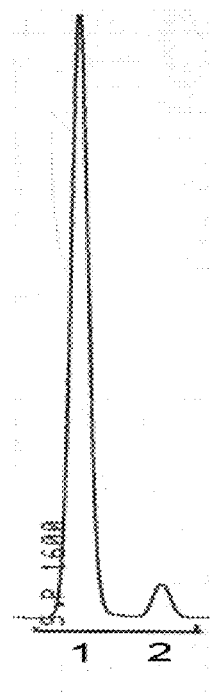
Figure 15:
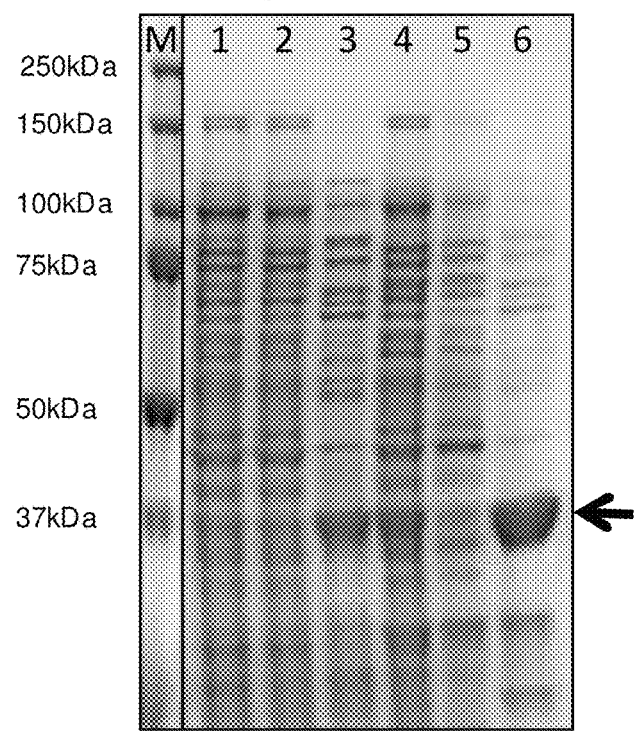

FIG. 1: 3-hydroxypropionate motif.
FIG. 2: Decarboxylation of mevalonate diphosphate by MDP decarboxylase—generic activity.
FIG. 3: Examples of 3-hydroxyalkanoates.
FIG. 4: Use of MDP decarboxylase for producing terminal alkenes.
FIG. 5: Cofactors that can be used in the reaction for purposes of structural complementation in the catalytic site.
FIG. 6: Integral method for producing an alkene from glucose.
FIG. 7: Chromatogram of the enzymatic reactions carried out in condition No. 1 of example 4.
FIG. 8: SDS-PAGE of the overexpression and purification steps of the enzyme SEQ ID NO: 6.
1. Markers
2. Culture before induction
3. Lysate
4. Fraction not adsorbed on the column
5. Column wash fraction
6. Purified enzyme, MW 36.8 kDa
FIG. 9: GC/MS chromatographic analysis of the conversion of HIV to IBN.
1 and 2: Negative controls corresponding to background noise in absence of enzyme.
3 and 4: Reactions in presence of enzyme SEQ ID NO: 6.
FIG. 10: Ratio of IBN production in presence and absence of ATP.
FIG. 11: Ratio of IBN production in presence and absence of $Mg^{2+}$.
FIG. 12: Enzymatic activity according to temperature. Ratio: amount of IBN formed in presence of enzyme versus background.
FIG. 13: IBN production according to concentration of HIV substrate.
FIG. 14: Measurement of optimized reaction and comparison with background. Measured by gas chromatography with flame ionization detection.
FIG. 15: Improved expression level by optimization of the nucleotide sequence coding SEQ ID NO: 6. Lane M: molecular weight markers.
Lanes 1, 2, 3: native nucleotide sequence
(1) Cell lysate, soluble fraction loaded on purification column
(2) Lysate fraction not retained on purification column
(3) Eluted fraction: 10 µg purified enzyme
Lanes 4, 5, 6: Optimized nucleotide sequence
(4) Cell lysate, soluble fraction loaded on purification column
(5) Lysate fraction not retained on purification column
(6) Eluted fraction: 10 µg purified enzyme

EXAMPLES

Example 1: Cloning and Expression of Several MDP Decarboxylases

The gene encoding MDP decarboxylase of *Saccharomyces cerevisiae* is synthesized from overlapping oligonucleotides and cloned in a pET plasmid (Novagen) allowing expression in bacteria. Said plasmid is then transformed by electroporation into bacterial strain BL21 (Invitrogen). The bacteria are streaked on a Petri dish containing ampicillin and incubated at 37° C. The next day, a bacterial colony is randomly selected and used to inoculate 50 ml of LB medium containing ampicillin. The culture is incubated for 24 h while shaking, after which the culture is centrifuged, the bacteria lysed by sonication, and a total protein extract prepared. An aliquot of the extract is loaded on an electrophoresis gel together with a protein extract from the same strain which has not been transformed, and with molecular weight markers. The lane corresponding to the transformed strain contains a single band of approximately 30 kD, which corresponds to the expected size of the protein, said band being absent in the lane loaded with the non-transformed bacteria.

Example 2: Measuring the Activity of the Protein Extracts Towards 3-hydroxy-3-methylbutyrate 3-hydroxy-3-methylbutyrate (Sigma, reference 55453 under the name β-hydroxyisovaleric acid), is suspended at a concentration of 10 g/l. Mevalonate diphosphate is synthesized from mevalonolactone and other reagents (Sigma) by the conventional method and resuspended at a concentration of 10 g/l.

Six chromatography vials are prepared. 50 μL buffer containing 50 mM Bistris/HCl 1 mM dithiothreitol, 10 mM $MgCl_2$ and 5 mM ATP are added to each vial.

Vials 1 and 4: 5 μl water are added (no substrate).
Vials 2 and 5: 5 μl of the mevalonate diphosphate preparation are added (positive control).
Vials 3 and 6: 5 μl of the 3-hydroxy-3-methylbutyrate (HIV) preparation are added.
Vials 1, 2 and 3: 5 μl of water are then added (no enzyme).
Vials 4, 5 and 6: 5 μl of the enzyme preparation described in example 1 are added.

Vials are sealed with a septum and crimped. All vials are incubated at 37° C. from 4 hours to 3 days. After incubation, a gas syringe is used to collect the gas present in each vial, and the $CO_2$ concentration in the samples is measured by gas chromatography. Vial 5 has a very high $CO_2$ concentration, and $CO_2$, at a lower concentration, is also detected in vial 6, which indicates a significant reaction of the enzyme preparation towards 3-hydroxy-3-methylbutyrate. The presence of isobutylene in the gas sample from vial 6 is then measured by gas chromatography with infrared or flame ionization detection.

Example 3: Optimization of Reaction Conditions by Using a Cofactor

The same reaction as that described in vial 6 of the previous example is carried out, but in one of the samples, ethyl diphosphate, synthesized to order, is added as cofactor.

In this example, three vials are used. The first contains buffers, ATP, and the enzyme extract in the amounts described in the previous example. The second vial contains the same components, but additionally contains 3-hydroxy-3-methylbutyrate in the amounts described in the previous example. The third vial contains, in addition to 3-hydroxy-3-methylbutyrate, 10 μl of 10 mg/l ethyl diphosphate.

As in the previous example, isobutylene formation is measured by gas chromatography with infrared or flame ionization detection. It is found that when ethyl diphosphate is present, the amount of isobutylene produced over time is markedly higher.

Example 4: Screening an Enzyme Library

A library of 63 genes encoding enzymes from the MDP decarboxylase family was obtained and tested for activity on HIV as substrate.

Cloning, Bacterial Cultures and Expression of Proteins.

The genes encoding the mevalonate diphosphate (MDP) decarboxylase family EC 4.1.1.33 were cloned in the pET 25b vector (Novagen) in the case of eukaryotic genes and pET 22b (Novagen) for genes of prokaryotic origin, with a 6-Histidine tag at the N-terminal end immediately after the methionine initiation codon. Competent E. coli BL21(DE3) cells (Novagen) were transformed with these vectors by heat shock. The cells were grown with shaking (160 rpm) at 30° C. in TB medium containing 0.5 M sorbitol, 5 mM betain, 100 μg/ml ampicillin until reaching an OD at 600 nm comprised between 0.8 and 1. Isopropyl-B-D-thiogalactopyranoside (IPTG) was then added to a final concentration of 1 mM and protein expression was continued at 20° C. overnight (approximately 16 h). The cells were collected by centrifugation at 4° C., 10,000 rpm for 20 min and the pellets were frozen at −80° C.

Cell Lysis 1.6 g of cells were thawed on ice and resuspended in 5 ml of 50 mM $Na_2HPO_4$ pH 8 containing 300 mM NaCl, 5 mM $MgCl_2$, 1 mM DTT. Twenty microliters of lysonase (Novagen) were added. Cells were incubated for 10 min at room temperature and then returned to ice for 20 min. Cell lysis was completed by sonication for 3×5 min in an ultrasound water bath at 0° C.; samples were homogenized between pulses. The bacterial extracts were then clarified by centrifugation at 4° C., 10,000 rpm for 20 min.

Protein Purification and Concentration (PROTINO Kit)

The clarified bacterial lysates were loaded on a PRO-TINO-1000 Ni-IDA column (Macherey-Nagel) allowing adsorption of 6-His tag proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated in Amicon Ultra-4 10 kDa cells (Millipore) to a final volume of 250 μl. Protein was quantified by the Bradford method.

Enzymatic Reactions

The desired enzymatic reaction (conversion of 3-hydroxy-3-methylbutyrate, or 3-hydroxyisovalerate, or else HIV) was tested in two experimental conditions that differed in terms of buffer and reaction pH.

Experimental Conditions No. 1.
100 mM citrate
10 mM $MgCl_2$
10 mM ATP
20 mM KCl-200
mM HIV
Final pH adjusted to 5.5
Experimental Conditions No. 2.
100 mM Tris-HCl pH 7.0
10 mM $MgCl_2$
10 mM ATP
20 mM KCl-200
200 mM HIV
Final pH adjusted to 7.0

The enzyme was added to the reaction mixture. As the protein yield was variable, the amount of enzyme added ranged between 0.01 and 1 mg/ml from one sample to another. The enzyme-free control reactions were carried out in parallel.

The 1 ml reactions were placed in 2 ml vials (Interchim) and sealed with teflon/silica/teflon septum (Interchim). Reactions were incubated without shaking at 37° C. for 72 h.

Analysis of Reactions

The gas present above the reactions was collected with a syringe equipped with a no-return mechanism. The gas sample was analyzed by gas chromatography (GC) coupled with mass spectrometry (MS). The instrument was previously calibrated using a range of isobutylene concentrations.
Column: BPX5 (SGE)
GC/MS: MSD 5973 (HP)

For each chromatogram, three principal peaks were obtained, the first corresponding to air, the second to water, and the third to isobutylene. Out of the 63 enzymes produced and tested, eleven potential candidates were identified in the primary screening. Some of these candidates are marked with an arrow in FIG. 7. Their identities are shown below, and their sequences in SEQ ID NO: 6 to 16 (His-tag not shown).

Candidate 1: SEQ ID NO: 7
Genebank accession number: CAI97800.1
Swissprot/TrEMBL accession number: Q1GAB2
Microorganisms: *Lactobacillus delbrueckii* subsp. *bulgaricus* (strain ATCC 11842/DSM 20081)
Candidate 2: SEQ ID NO: 8
Genebank accession number: CAJ51653
Swissprot/TrEMBL accession number: Q18K00
Microorganisms: *Haloquadratum walsbyi* DSM 16790
Candidate 3: SEQ ID NO: 9
Genebank accession number: ABD99494.1
Swissprot/TrEMBL accession number: Q1WU41
Microorganisms: *Lactobacillus salivarius* subsp. *salivarius* (strain UCC118)
Candidate 4: SEQ ID NO: 10
Genebank accession number: ABJ57000.1
Swissprot/TrEMBL accession number: Q04EX2
Microorganisms: *Oenococcus oeni* (strain BAA-331/PSU-1)
Candidate 5: SEQ ID NO: 11
Genebank accession number: ABJ67984.1
Swissprot/TrEMBL accession number: Q03FN8
Microorganisms: *Pediococcus pentosaceus* ATCC 25745
Candidate 6: SEQ ID NO: 12
Genebank accession number: ABV09606.1
Swissprot/TrEMBL accession number: A8AUU9
Microorganisms: *Streptococcus gordonii* (strain Challis/ATCC 35105/CH1/DL1/V288)
Candidate 7: SEQ ID NO: 13
Genebank accession number: ABQ14154.1
Swissprot/TrEMBL accession number: A5EVP2
Microorganisms: *Dichelobacter nodosus* VCS1703A
Candidate 8: SEQ ID NO: 14
Genebank accession number: EDT95457.1
Swissprot/TrEMBL accession number: B2DRT0
Microorganisms: *Streptococcus pneumoniae* CDC0288-04
Candidate 9: SEQ ID NO: 15
Genebank accession number: AAT86835
Swissprot/TrEMBL accession number: Q5XCM8
Microorganisms: *Streptococcus pyogenes* serotype M6 (ATCC BAA-946/MGAS10394)
Candidate 10: SEQ ID NO: 6
Genebank accession number: AAT43941
Swissprot/TrEMBL accession number: Q6KZB1
Microorganisms: *Picrophilus torridus* DSM 9790
Candidate 11: SEQ ID NO: 16
Genebank accession number: AAV43007.1
Swissprot/TrEMBL accession number: Q5FJW7
Microorganisms: *Lactobacillus acidophilus* NCFM The highest levels of isobutylene (IBN) production were observed with candidate 10, that is, with the purified decarboxylase enzyme of SEQ ID NO: 6 from *Picrophilus torridus*. This enzyme was retained for further characterization.

Example 5: Characterization of Enzyme SEQ ID NO: 6

The recombinant enzyme was purified as described in example 4. The results, presented in FIG. 8, show that enzyme purity in the final protein sample was approximately 90%.

The activity of the isolated enzyme was confirmed. The reaction was carried out in the following conditions:
100 mM Tris-HCl pH 7.0
10 mM $MgCl_2$
10 mM ATP
20 mM KCl
250 M HIV
Final pH adjusted to 6.0
3 mg/ml enzyme After 72 h incubation at 30° C., the signal was measured by GC/MS. The results are shown in FIG. 9. In the presence of the enzyme, IBN production was increased here by approximately 2.3-fold over background noise. The background noise observed here is in agreement with the organic chemistry literature, showing that in aqueous solution and at a temperature of around 100° C., 3-hydroxyisovaleric acid slowly decarboxylates to tert-butanol, which is partially dehydrated to isobutylene, following an equilibrium favorable to the formation of tert-butanol (Pressman and Luca, J. Am. Chem. Soc. 1940).

Effect of ATP Co-Substrate
Test Conditions
100 mM citrate
50 mM KCl
10 mM $MgCl_2$
200 mM HIV (to be specified)
1 mg/ml purified enzyme
pH 5.5
Incubation 72 h at 30° C.

| Conditions | ATP final concentration | Enzyme |
| --- | --- | --- |
| 1 | 0 mM | 0 mg/ml |
| 2 | 0 mM | 1 mg/ml |
| 3 | 10 mM | 0 mg/ml |
| 4 | 10 mM | 1 mg/ml |

The results in FIG. 10 show that enzyme activity was only observed in the presence of the co-substrate ATP. Other molecules, and in particular those containing a phosphoanhydride bond, could also be efficient co-substrates for the enzyme.

Effect of $Mg^{2+}$ Cofactor
Test Conditions
100 mM citrate pH 5.5
50 mM KCl
10 mM ATP
200 mM HIV (to be specified)
pH 5.5

1 mg/ml purified enzyme
Incubation 72 h at 30° C.

| Conditions | MgCl₂ final concentration | Enzyme |
|---|---|---|
| 1 | 0 mM | 0 mg/ml |
| 2 | 0 mM | 1 mg/ml |
| 3 | 5 mM | 0 mg/ml |
| 4 | 5 mM | 1 mg/ml |

The results in FIG. 11 show that enzyme activity was improved in the presence of $Mg^{2+}$ ions. Other ions, and in particular other divalent ions, could be used as cofactor in place of or in addition to $Mg^{2+}$ ions.

Enzymatic Activity According to Temperature
Test Conditions
100 mM buffer
50 mM KCl
10 mM ATP
200 mM HIV (to be specified)
1 mg/ml purified enzyme
Incubation 72 h at different temperatures.

The results in FIG. 12 show that the enzyme is moderately thermoactive with a temperature optimum of approximately 50° C.

Activity According to pH
Test Conditions
100 mM buffer
50 mM KCl
10 mM ATP
200 mM HIV (to be specified)
1 mg/ml purified enzyme
Incubation 72 h at 30° C.

Optimal conditions were obtained with a pH of 5.5 in 100 mM citrate.

Enzyme Parameters

A substrate range was tested in the previously described conditions, with incubation at 50° C. The Km of the enzyme is approximately 40 mM HIV.

Optimization of Reaction Conditions

Optimum reaction conditions were sought, and the following conditions were retained:
100 mM citrate
50 mM KCl
40 mM ATP
200 mM HIV
1 mg/ml enzyme
Incubation 48 h at 50° C.

As shown in FIG. 14, the ratio of the signal over-background noise is approximately 100.

Example 6: Optimization of *P. torridus* MDP Decarboxylase Expression in *E. coli*

The initial level of expression in *E. coli* BL21 was low, as the band was difficult to see on SDS-PAGE before purification. The Codon Optimization Index (CAI) of the native sequence for expression in *E. coli* was measured with the "Optimizer" program available at http://genomes.urv.es/OP-TIMIZER/, and based on the method of Sharp and Li (1987). The value obtained was only 0.23, reflecting the low level of expression of the protein in *E. coli*.

A sequence coding for an identical protein, but containing codons better adapted for expression in *E. coli*, was generated. This sequence had a CAI of 0.77 which is closer to the optimum of 1. The native sequence and the optimized sequence are shown in SEQ ID NO: 17 (optimized sequence of *P. torridus* (AAT43941) MDP decarboxylase including the His Tag) and SEQ ID NO: 19 (native sequence of *P. torridus* (AAT43941) MDP decarboxylase including the His Tag). The optimized sequence was synthesized by oligonucleotide concatenation and cloned in a pET25 expression vector. After transformation of the vector into *E. coli* strain BL21(DE3) and induction according to the previously described protocol, the proteins were produced, purified and analyzed on a gel as described previously. The same protocol was carried out with the native sequence for purposes of comparison.

Comparison of expression levels of candidate 224 using either the native nucleotide sequence or the sequence optimized for expression in *E. coli*.

The results in FIG. 15 show that the protein corresponding to the optimized gene was clearly visible on the gel in the non-purified cell lysate (lane 4), which indicates a very notable increase in expression. The level of purity of the protein after the purification step was also higher in the case of the optimized gene.

Activity was measured on the crude lysate. No activity was detected on the crude lysate corresponding to the native nucleic sequence. The expression of the protein was improved such that the crude lysate obtained with the improved sequence (optimized clone 224) now displayed this activity.

The following reaction medium was used in this test:
Reaction Medium

| Products | Final concentration |
|---|---|
| Acetate reaction buffer (500 mM, pH 5.5) | 50 mM |
| MgCl₂ (1M) | 10 mM |
| KCl (1M) | 20 mM |
| HIV (3M) | 50 mM |
| ATP (100 mM) | 40 mM |
| Protease inhibitor (100X) | 1X |
| H20 | |
| Enzyme | 89 µg total protein (crude lysate) |

Incubation 2 days at 50° C.
Results
Condition No. 1: Lysate of optimized clone 224
Condition No. 2: Lysate of clone GB6 (empty pET plasmid)

| Conditions | Signal area surface | Ratio |
|---|---|---|
| 1 | 1083 | 22 |
| 2 | 49 | |

Example 7: Method for Synthesizing Isobutylene from 3-Hydroxy-3-Methylbutyrate and Conversion to Isooctane A reaction identical to that of vial 3 in example 3 was carried out in a 1 liter volume, in a fermenter equipped with a gas extraction system. The presence of the recombinant enzyme induced the conversion of 3-hydroxy-3-methylbutyrate to isobutylene, which naturally degasses, and which was recovered by a gas extraction system located in the upper part of the fermenter. Isobutylene was then used to produce isooctene by addition catalyzed by Amberlyst 35wet or 36wet resin (Rohm and Haas). Isooctene was reduced in turn to isooctane by catalytic hydrogenation.

Example 8: Enzyme Engineering to Improve Efficacy for Substrates

Random mutagenesis technology was used to create a library containing thousands of mutants of the gene described in example 1. This mutant library was then cloned in the expression plasmid and transformed into competent bacterial strain BL21.

A thousand bacteria were then isolated and inoculated into Eppendorf tubes containing 500 µl LB medium supplemented with ampicillin. The samples were incubated on a shaker for 15 h. The next day, the amount of isobutylene produced was determined by using one or another of the experimental protocols described in the previous examples.

Clones with a significantly increased amount of isobutylene were then revalidated using the same experimental protocol. Once this improvement was validated, the plasmid was extracted from each improved clone and sequenced. Mutations responsible for the improved activity were identified and combined on a same plasmid. The plasmid containing the different improving mutations was in turn transformed into competent bacteria, and the same analysis was carried out.

The clone containing the combined mutations, which had significantly greater activity than the one containing only a single improving mutation, was then used as the basis for a new cycle of mutation/screening, to identify mutants with even further improved activity.

On completion of this protocol, the clone containing several mutations and having the best activity was selected.

Example 9: Method for Synthesizing Ethylene from 3-hydroxypropionate

The gene encoding the enzyme described in example 1 was inserted in a plasmid allowing expression of the recombinant proteins in an *E. coli* strain. The plasmid was transformed into the bacteria of said strain. The transformed bacteria were then incubated in a fermenter in the presence of propyl diphosphate (10 mg/l) and 3-hydroxypropionate (1 g/l). The presence of the recombinant enzyme led to the conversion of 3-hydroxypropionate to ethylene, which spontaneously degasses, and which was recovered by a gas extraction system located in the upper part of the fermenter. Ethylene was then measured in the gas sample by gas chromatography with infrared detection in the part of the spectrum where ethylene emits strongly.

Example 10: Method for Synthesizing Propylene from 3-hydroxybutyrate

The gene encoding the enzyme described in example 1 or an enzyme described in example 4 was inserted in a plasmid allowing expression of recombinant proteins in an *E. coli* strain. The plasmid was transformed into the bacteria of said strain. The transformed bacteria were then incubated in a fermenter in the presence of ethyl diphosphate (10 mg/l) and 3-hydroxybutyrate (1 g/l) (Sigma, reference 166898). The presence of the recombinant enzyme led to the conversion of 3-hydroxybutyrate to propylene, which spontaneously degasses, and which was recovered by a gas extraction system located in the upper part of the fermenter. Propylene was then measured in the gas sample by gas chromatography with infrared detection in the part of the spectrum where propylene emits strongly.

Example 11: Method for Synthesizing Propylene from Glucose

The gene encoding the enzyme described in example 1 or an enzyme described in example 4 was cloned in a plasmid allowing expression of recombinant proteins in the bacterium *Alcaligenes eutrophus*. The plasmid was transformed into the bacteria of said strain.

The transformed bacteria were then incubated in a fermenter in the presence of glucose and ethyl diphosphate and in microaerophilic conditions, then subjected to heat shock which induced them to produce large quantities of 3-hydroxybutyrate. The presence of the recombinant enzyme led to the simultaneous conversion of 3-hydroxybutyrate to propylene, which spontaneously degasses, and which was recovered by a gas extraction system located in the upper part of the fermenter.

Example 12: Method for Synthesizing Propylene from Glucose

This example describes a method very similar to that of example 11. The main difference consists in the use of an *E. coli* strain modified so as to produce 3-hydroxybutyrate instead of a natural strain like *Alcaligenes eutrophus*. Said strain was obtained by the engineering of metabolic pathways so as to lead to accumulation of 3-hydroxybutyrate. Addition of an MDP decarboxylase such as described in example 1 or in example 4 enabled the conversion of 3-hydroxybutyrate to propylene.

Example 13: Method for Synthesizing Isobutylene from Glucose

The gene encoding the enzyme described in example 1 was inserted in a plasmid allowing expression of recombinant proteins in *E. coli* strains that had also undergone metabolic modifications so that they endogenously synthesized 3-hydroxy-3-methylbutyrate.

The bacteria were then incubated in a fermenter in the presence of glucose and in microaerophilic conditions. The presence of the recombinant enzyme induces the simultaneous conversion of 3-hydroxy-3-methylbutyrate to isobutylene, which naturally degasses, and which was recovered by a gas extraction system located in the upper part of the fermenter.

The invention claimed is:

1. A method for producing a terminal alkene, comprising converting a 3-hydroxyalkanoate into a terminal alkene in a microorganism comprising a recombinantly expressed mevalonate diphosphate (MDP) decarboxylase enzyme in the presence of a co-substrate containing a phosphoanhydride bond, wherein the 3-hydroxyalkanoate is a molecule comprising 3-hydroxypropionate as a common motif and optionally one or two alkyl substitutions on carbon 3.

2. The method according to claim 1, wherein the terminal alkene comprises a linear or branched alkyl group at carbon 2.

3. The method according to claim 1, wherein the 3-hydroxyalkanoate is 3-hydroxybutyrate and the terminal alkene is propylene.

4. The method according to claim 1, wherein the 3-hydroxyalkanoate is 3-hydroxyvalerate and the terminal alkene is 1-butylene.

5. The method according to claim 1, wherein the 3-hydroxyalkanoate is 3-hydroxy-3-methylbutyrate and the terminal alkene is isobutylene.

6. The method according to claim 1, wherein the 3-hydroxyalkanoate is 3-hydroxy-3-methylvalerate and the terminal alkene is isoamylene.

7. The method according to claim 1, wherein the MDP decarboxylase enzyme comprises an amino acid sequence selected from SEQ ID NO: 1-16.

8. The method according to claim 1, wherein the method further comprises adding a cofactor containing a phosphoanhydride motif to the reaction, wherein the cofactor has the general formula R—O—PO$_2$H—O—PO$_3$H$_2$ in which R is a hydrogen atom, a methyl, ethyl or propyl group, any linear, branched or cyclic alkyl group, or any other monovalent organic group.

9. The method according to claim 1, further comprising adding a methylene diphosphonate monoester to the reaction, wherein the methylene diphosphonate monoester has the general formula R—O—PO$_2$H—CH$_2$—PO$_3$H$_2$ in which R is a hydrogen atom, a methyl, ethyl or propyl group, any linear, branched or cyclic alkyl group, or any other monovalent organic group.

10. The method according to claim 1, wherein the microorganism overexpresses said MDP decarboxylase enzyme.

11. The method according to claim 1, wherein the method is carried out by a microorganism which endogenously produces one or more 3-hydroxyalkanoates, and which also expresses or overexpresses said MDP decarboxylase enzyme, so as to produce terminal alkenes directly from a carbon source.

12. The method according to claim 11, wherein the microorganism is a bacterium of strain *Alcaligenes eutrophus* or *Bacillus megaterium*, or a bacterium, yeast or fungus which recombinantly overproduces one or more 3-hydroxyalkanoates.

13. The method according to claim 11, wherein the carbon source is glucose or any other hexose, xylose or any other pentose, glycerol or any other polyol, starch, cellulose, hemicellulose, a poly-3-hydroxyalkanoate or any other polymer, the method then being carried out in the presence of a system for degrading said polymer to monomer.

14. The method according to claim 11, wherein the microorganism is a photosynthetic microorganism which endogenously produces one or more 3-hydroxyalkanoates, and further overexpressing the MDP decarboxylase enzyme, so as to produce terminal alkenes directly from CO$_2$ present in solution.

15. The method according to claim 1, wherein the 3-hydroxyalkanoate is produced by a first microorganism that converts a carbon source to 3-hydroxyalkanoate, and the conversion is catalyzed by said MDP decarboxylase enzyme which is isolated or expressed by a second microorganism, allowing the conversion of the 3-hydroxyalkanoate to the terminal alkene.

16. A method according to claim 1, further comprising a step of collecting gas of terminal alkenes degassing from the reaction.

17. The method according to claim 1, wherein the method is carried out in microaerophilic conditions.

18. The method of claim 1, wherein the co-substrate is adenosine triphosphate (ATP), a ribonucleoside triphosphate (rNTP), a deoxyribonucleoside triphosphate (dNTP) or a mixture of several of such triphosphates, a polyphosphate, or a pyrophosphate.

19. The method according to claim 5, wherein the MDP decarboxylase enzyme comprises an amino acid sequence selected from SEQ ID NO: 1-16.

20. The method of claim 19, wherein the method further comprises adding a cofactor containing a phosphoanhydride motif to the reaction, wherein the cofactor has the general formula R—O—PO$_2$H—O—PO$_3$H$_2$ in which R is a hydrogen atom, a methyl, ethyl or propyl group, any linear, branched or cyclic alkyl group, or any other monovalent organic group.

21. The method according to claim 19, further comprising adding a methylene diphosphonate monoester to the reaction, wherein the methylene diphosphonate monoester has the general formula R—O—PO$_2$H—CH$_2$—PO$_3$H$_2$ in which R is a hydrogen atom, a methyl, ethyl or propyl group, any linear, branched or cyclic alkyl group, or any other monovalent organic group.

22. The method according to claim 19, wherein the microorganism overexpresses said MDP decarboxylase enzyme.

23. The method according to claim 19, wherein the method is carried out by a microorganism which endogenously produces 3-hydroxy-3-methylbutyrate, and which also expresses or overexpresses said MDP decarboxylase enzyme, so as to produce isobutylene directly from a carbon source.

24. The method according to claim 23, wherein the microorganism is a bacterium of strain *Alcaligenes eutrophus* or *Bacillus megaterium*, or a bacterium, yeast or fungus which recombinantly overproduces 3-hydroxy-3-methylbutyrate.

25. The method according to claim 23, wherein the carbon source is glucose or any other hexose, xylose or any other pentose, glycerol or any other polyol, starch, cellulose, hemicellulose, a poly-3-hydroxyalkanoate or any other polymer, the method then being carried out in the presence of a system for degrading said polymer to monomer.

26. The method according to claim 23, wherein the microorganism is a photosynthetic microorganism which endogenously produces 3-hydroxy-3-methylbutyrate, and further overexpressing the MDP decarboxylase enzyme, so as to produce isobutylene directly from CO$_2$ present in solution.

27. The method according to claim 19, wherein 3-hydroxy-3-methylbutyrate is produced by a first microorganism that converts a carbon source to 3-hydroxy-3-methylbutyrate, and the conversion is catalyzed by said MD P decarboxylase enzyme which is isolated or expressed by a second microorganism, allowing the conversion of the 3-hydroxy-3-methylbutyrate to isobutylene.

28. A method according to claim 19, further comprising a step of collecting gas of isobutylene degassing from the reaction.

29. The method according to claim 19, wherein the method is carried out in microaerophilic conditions.

30. The method of claim 19, wherein the co-substrate is adenosine triphosphate (ATP), a ribonucleoside triphosphate (rNTP), a deoxyribonucleoside triphosphate (dNTP) or a mixture of several of such triphosphates, a polyphosphate, or a pyrophosphate.

31. The method of claim 2, wherein the MDP decarboxylase enzyme comprises an amino acid sequence selected from SEQ ID NO: 1-16.

32. The method of claim 3, wherein the MDP decarboxylase enzyme comprises an amino acid sequence selected from SEQ ID NO: 1-16.

33. The method of claim 4, wherein the MDP decarboxylase enzyme comprises an amino acid sequence selected from SEQ ID NO: 1-16.

34. The method of claim 6, wherein the MDP decarboxylase enzyme comprises an amino acid sequence selected from SEQ ID NO: 1-16.

* * * * *

SEQUENCE LISTING

<160> NUMBER OF SEQ ID NOS: 20

<210> SEQ ID NO 1
<211> LENGTH: 400
<212> TYPE: PRT

<213> ORGANISM: Homo sapiens

<400> SEQUENCE: 1

Met Ala Ser Glu Lys Pro Leu Ala Ala Val Thr Cys Thr Ala Pro Val
1               5                   10                  15

Asn Ile Ala Val Ile Lys Tyr Trp Gly Lys Arg Asp Glu Glu Leu Val
            20                  25                  30

Leu Pro Ile Asn Ser Ser Leu Ser Val Thr Leu His Gln Asp Gln Leu
        35                  40                  45

Lys Thr Thr Thr Thr Ala Val Ile Ser Lys Asp Phe Thr Glu Asp Arg
    50                  55                  60

Ile Trp Leu Asn Gly Arg Glu Glu Asp Val Gly Gln Pro Arg Leu Gln
65                  70                  75                  80

Ala Cys Leu Arg Glu Ile Arg Cys Leu Ala Arg Lys Arg Arg Asn Ser
                85                  90                  95

Arg Asp Gly Asp Pro Leu Pro Ser Ser Leu Ser Cys Lys Val His Val
            100                 105                 110

Ala Ser Val Asn Asn Phe Pro Thr Ala Ala Gly Leu Ala Ser Ser Ala
        115                 120                 125

Ala Gly Tyr Ala Cys Leu Ala Tyr Thr Leu Ala Arg Val Tyr Gly Val
    130                 135                 140

Glu Ser Asp Leu Ser Glu Val Ala Arg Arg Gly Ser Gly Ser Ala Cys
145                 150                 155                 160

Arg Ser Leu Tyr Gly Gly Phe Val Glu Trp Gln Met Gly Glu Gln Ala
                165                 170                 175

Asp Gly Lys Asp Ser Ile Ala Arg Gln Val Ala Pro Glu Ser His Trp
            180                 185                 190

Pro Glu Leu Arg Val Leu Ile Leu Val Val Ser Ala Gly Lys Lys Leu
        195                 200                 205

Thr Gly Ser Thr Val Gly Met Arg Ala Ser Val Glu Thr Ser Pro Leu
    210                 215                 220

Leu Arg Phe Arg Ala Glu Ser Val Val Pro Ala Arg Met Ala Glu Met
225                 230                 235                 240

Ala Arg Cys Ile Arg Glu Arg Asp Phe Pro Ser Phe Ala Gln Leu Thr
                245                 250                 255

Met Lys Asp Ser Asn Gln Phe His Ala Thr Cys Leu Asp Thr Phe Pro
            260                 265                 270

Pro Ile Ser Tyr Leu Asn Ala Ile Ser Trp Arg Ile Ile His Leu Val
        275                 280                 285

His Arg Phe Asn Ala His His Gly Asp Thr Lys Val Ala Tyr Thr Phe
    290                 295                 300

Asp Ala Gly Pro Asn Ala Val Ile Phe Thr Leu Asp Asp Thr Val Ala
305                 310                 315                 320

Glu Phe Val Ala Ala Val Trp His Gly Phe Pro Pro Gly Ser Asn Gly
                325                 330                 335

Asp Thr Phe Leu Lys Gly Leu Gln Val Arg Pro Ala Pro Leu Ser Ala
            340                 345                 350

Glu Leu Gln Ala Ala Leu Ala Met Glu Pro Thr Pro Gly Gly Val Lys
        355                 360                 365

Tyr Ile Ile Val Thr Gln Val Gly Pro Gly Pro Gln Ile Leu Asp Asp
    370                 375                 380

Pro Cys Ala His Leu Leu Gly Pro Asp Gly Leu Pro Lys Pro Ala Ala
385                 390                 395                 400

```
<210> SEQ ID NO 2
<211> LENGTH: 396
<212> TYPE: PRT
<213> ORGANISM: Saccharomyces cerevisiae

<400> SEQUENCE: 2

Met Thr Val Tyr Thr Ala Ser Val Thr Ala Pro Val Asn Ile Ala Thr
 1               5                  10                  15

Leu Lys Tyr Trp Gly Lys Arg Asp Thr Lys Leu Asn Leu Pro Thr Asn
             20                  25                  30

Ser Ser Ile Ser Val Thr Leu Ser Gln Asp Asp Leu Arg Thr Leu Thr
         35                  40                  45

Ser Ala Thr Ala Pro Glu Phe Glu Arg Asp Thr Leu Trp Leu Asn
 50                  55                  60

Gly Glu Pro His Ser Ile Asp Asn Glu Arg Thr Gln Asn Cys Leu Arg
 65                  70                  75                  80

Asp Leu Arg Gln Leu Arg Lys Glu Met Glu Ser Lys Asp Ala Ser Leu
             85                  90                  95

Pro Thr Leu Ser Gln Trp Lys Leu His Ile Val Ser Glu Asn Asn Phe
            100                 105                 110

Pro Thr Ala Ala Gly Leu Ala Ser Ala Ala Gly Phe Ala Ala Leu
            115                 120                 125

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
            195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
            355                 360                 365

Arg Val Ile Leu Thr Gln Val Gly Ser Gly Pro Gln Glu Thr Asn Glu
370                 375                 380
```

```
Ser Leu Ile Asp Ala Lys Thr Gly Leu Pro Lys Glu
385                 390             395
```

<210> SEQ ID NO 3
<211> LENGTH: 404
<212> TYPE: PRT
<213> ORGANISM: Aspergillus niger

<400> SEQUENCE: 3

```
Met Ala Ala Ser Ala Asp Ser Gln Val Phe Arg Ala Thr Thr Thr Ala
1               5                   10                  15

Pro Val Asn Ile Ala Val Ile Lys Tyr Trp Gly Lys Arg Asp Ala Val
                20                  25                  30

Leu Asn Leu Pro Thr Asn Ser Ser Leu Ser Val Thr Leu Ser Gln Arg
            35                  40                  45

Ser Leu Arg Thr Leu Thr Thr Ala Ser Cys Ala Pro Phe Tyr Pro Ala
50                  55                  60

Lys Asp Glu Leu Thr Leu Asn Gly Lys Pro Gln Asp Ile Gln Ser Ser
65                  70                  75                  80

Lys Arg Thr Leu Ala Cys Leu Ala Ser Leu Arg Ala His Arg Arg Glu
                85                  90                  95

Leu Glu Asp Ala Asn Pro Ser Leu Pro Lys Leu Ser Ser Phe Pro Leu
            100                 105                 110

Arg Ile Val Ser Glu Asn Asn Phe Pro Thr Ala Ala Gly Leu Ala Ser
            115                 120                 125

Ser Ala Ala Gly Phe Ala Ala Leu Val Arg Ala Val Ala Asp Leu Tyr
130                 135                 140

Gln Leu Pro Gln Ser Pro Arg Asp Leu Ser Arg Ile Ala Arg Gln Gly
145                 150                 155                 160

Ser Gly Ser Ala Cys Arg Ser Leu Met Gly Gly Tyr Val Ala Trp Arg
                165                 170                 175

Ala Gly Ser Leu Glu Asp Gly Ser Asp Ser Leu Ala Glu Glu Val Ala
            180                 185                 190

Pro Gln Ser His Trp Pro Glu Met Arg Ala Leu Ile Leu Val Val Ser
            195                 200                 205

Ala Ala Lys Lys Asp Val Pro Ser Thr Glu Gly Met Gln Thr Thr Val
210                 215                 220

Ala Thr Ser Asn Leu Phe Ala Thr Arg Ala Ser Thr Val Val Pro Glu
225                 230                 235                 240

Arg Met Ala Ala Ile Glu Thr Ala Ile Gln Asn Arg Asp Phe Pro Ala
                245                 250                 255

Phe Ala Glu Ile Thr Met Arg Asp Ser Asn Ser Phe His Ala Thr Cys
            260                 265                 270

Leu Asp Ser Trp Pro Pro Ile Phe Tyr Met Asn Asp Val Ser Arg Ala
            275                 280                 285

Ala Val Arg Leu Val His Asp Ile Asn Arg Ala Ile Gly Arg Thr Val
290                 295                 300

Cys Ala Tyr Thr Tyr Asp Ala Gly Pro Asn Ala Val Ile Tyr Tyr Leu
305                 310                 315                 320

Glu Lys Asp Thr Glu Leu Val Ala Gly Thr Val Lys Ala Ile Leu Gly
                325                 330                 335

Glu Lys Thr Glu Gly Trp Glu Gly Pro Phe Tyr Thr Pro Leu Lys Asp
            340                 345                 350

Val Thr Thr Pro Gly Val Ser Leu Asp Glu Ile Asp Pro Arg Thr Val
```

```
              355                 360                 365
Glu Ser Leu Lys Asp Gly Val Ser Arg Val Ile Leu Thr Gly Val Gly
370                 375                 380

Glu Gly Pro Ile Ser Val Asp Gln His Leu Val Ser Glu Lys Gly Asp
385                 390                 395                 400

Ile Leu Ser Ala

<210> SEQ ID NO 4
<211> LENGTH: 325
<212> TYPE: PRT
<213> ORGANISM: Lactobacillus plantarum

<400> SEQUENCE: 4

Met Lys Thr Val Thr Ala Lys Ala His Thr Asn Ile Ala Leu Val Lys
1               5                  10                  15

Tyr Trp Gly Lys Lys Asp Ala Ala Leu Met Leu Pro Gln Asn Gly Ser
                20                  25                  30

Ile Ser Leu Thr Leu Asp His Phe Tyr Thr Gln Thr Ser Val Thr Phe
            35                  40                  45

Asp Glu His Leu Asp Thr Asp Gln Ile Tyr Phe Asn His Gln His Leu
50                  55                  60

Pro Thr Gly Lys Ser Ala Arg Ile Ser Gln Phe Leu Asp Leu Ile Arg
65                  70                  75                  80

Gln Arg Ser Gly Gln Thr Asn Tyr Ala Thr Val Lys Thr Glu Asn His
                85                  90                  95

Val Pro Thr Ser Ala Gly Leu Ala Ser Ser Ala Ser Gly Phe Ala Ala
            100                 105                 110

Leu Ala Gly Ala Ala Ser Arg Ala Ala Gly Leu Gln Leu Asp Ala Ala
        115                 120                 125

Asp Leu Ser Arg Leu Ala Arg Arg Gly Ser Gly Ser Ala Thr Arg Ser
130                 135                 140

Ile Phe Gly Gly Phe Val Glu Trp His Ala Gly His Asp Asp Gln Ser
145                 150                 155                 160

Ser Tyr Ala Glu Val Leu Gln Asp Pro Val Asp Trp Asp Ile Gln Met
                165                 170                 175

Ile Ala Val Val Leu Lys Ala Thr Lys Lys Thr Ile Ser Ser Thr Asp
            180                 185                 190

Gly Met Ala Arg Val Val Ala Thr Ser Pro Tyr Tyr Pro Ala Trp Ile
        195                 200                 205

Thr Thr Ala Glu Thr Asp Leu Lys Arg Met Arg Gln Ala Ile Ala Asp
210                 215                 220

Arg Asp Leu Thr Thr Val Gly Gln Ile Ala Glu Thr Asn Ala Met Arg
225                 230                 235                 240

Met His Ala Leu Asn Leu Ser Ala Glu Pro Ala Phe Asn Tyr Phe Thr
                245                 250                 255

Ala Asp Thr Leu Thr Ala Ile Gln Ala Val Asn Asp Leu Arg Ser His
            260                 265                 270

Gly Ile Asn Cys Tyr Tyr Thr Leu Asp Ala Gly Pro Asn Val Lys Ile
        275                 280                 285

Ile Cys Ala Gly Gln Asp Thr Asp Thr Ile Met Thr Gly Leu Gln Gln
        290                 295                 300

His Phe Asp Ala Asp Gln Leu Ile Val Ala Lys Pro Gly Pro Gly Ile
305                 310                 315                 320

Thr Ile Thr Glu Lys
```

<210> SEQ ID NO 5
<211> LENGTH: 314
<212> TYPE: PRT
<213> ORGANISM: Streptococcus pyrogenes

<400> SEQUENCE: 5

```
Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr Ser Asp Gln Phe Tyr Ile Asn Gly
    50                  55                  60

Ile Leu Gln Asn Asp Glu Glu His Thr Lys Ile Ser Ala Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asp Thr Gln Leu Asp Gln
        115                 120                 125

Lys Ala Leu Ala Gln Lys Ala Lys Phe Ala Ser Gly Ser Ser Ser Arg
    130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Gln Trp Val Gln Ser Ala Ile
        195                 200                 205

Asp Tyr Gln His Met Leu Thr Tyr Leu Lys Thr Asn Asn Phe Glu Lys
    210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Gly Phe Ala Cys Tyr
            260                 265                 270

Phe Thr Met Asp Ala Gly Pro Asn Val Lys Val Leu Cys Leu Glu Lys
        275                 280                 285

Asp Leu Ala Gln Leu Ala Glu Arg Leu Gly Lys Asn Tyr Arg Ile Ile
    290                 295                 300

Val Ser Lys Thr Lys Asp Leu Pro Asp Val
305                 310
```

<210> SEQ ID NO 6
<211> LENGTH: 324
<212> TYPE: PRT
<213> ORGANISM: Picrophilus torridus

<400> SEQUENCE: 6

```
Met Glu Asn Tyr Asn Val Lys Thr Arg Ala Phe Pro Thr Ile Gly Ile
```

```
           1               5                  10                 15
         Ile Leu Leu Gly Gly Ile Ser Asp Lys Lys Asn Arg Ile Pro Leu His
                         20                 25                 30
         Thr Thr Ala Gly Ile Ala Tyr Thr Gly Ile Asn Asn Asp Val Tyr Thr
                         35                 40                 45
         Glu Thr Lys Leu Tyr Val Ser Lys Asp Glu Lys Cys Tyr Ile Asp Gly
              50                 55                 60
         Lys Glu Ile Asp Leu Asn Ser Asp Arg Ser Pro Ser Lys Val Ile Asp
         65                 70                 75                 80
         Lys Phe Lys His Glu Ile Leu Met Arg Val Asn Leu Asp Asp Glu Asn
                         85                 90                 95
         Asn Leu Ser Ile Asp Ser Arg Asn Phe Asn Ile Leu Ser Gly Ser Ser
                         100                105                110
         Asp Ser Gly Ala Ala Leu Gly Glu Cys Ile Glu Ser Ile Phe Glu
                         115                120                125
         Tyr Asn Ile Asn Ile Phe Thr Phe Glu Asn Asp Leu Gln Arg Ile Ser
                         130                135                140
         Glu Ser Val Gly Arg Ser Leu Tyr Gly Gly Leu Thr Val Asn Tyr Ala
         145                150                155                160
         Asn Gly Arg Glu Ser Leu Thr Glu Pro Leu Leu Glu Pro Glu Ala Phe
                         165                170                175
         Asn Asn Phe Thr Ile Ile Gly Ala His Phe Asn Ile Asp Arg Lys Pro
                         180                185                190
         Ser Asn Glu Ile His Glu Asn Ile Ile Lys His Glu Asn Tyr Arg Glu
                         195                200                205
         Arg Ile Lys Ser Ala Glu Arg Lys Ala Lys Leu Glu Glu Leu Ser
                         210                215                220
         Arg Asn Ala Asn Ile Lys Gly Ile Phe Glu Leu Ala Glu Ser Asp Thr
         225                230                235                240
         Val Glu Tyr His Lys Met Leu His Asp Val Gly Val Asp Ile Ile Asn
                         245                250                255
         Asp Arg Met Glu Asn Leu Ile Glu Arg Val Lys Glu Met Lys Asn Asn
                         260                265                270
         Phe Trp Asn Ser Tyr Ile Val Thr Gly Gly Pro Asn Val Phe Val Ile
                         275                280                285
         Thr Glu Lys Lys Asp Val Asp Lys Ala Met Glu Gly Leu Asn Asp Leu
                         290                295                300
         Cys Asp Asp Ile Arg Leu Leu Lys Val Ala Gly Lys Pro Gln Val Ile
         305                310                315                320
         Ser Lys Asn Phe

<210> SEQ ID NO 7
<211> LENGTH: 319
<212> TYPE: PRT
<213> ORGANISM: Lactobacillus delbrueckii
<221> NAME/KEY:
<223> OTHER INFORMATION: /sub-species = bulgaricus

<400> SEQUENCE: 7

Met Ser Lys Thr Ala Arg Ala His Thr Asn Ile Ala Leu Ile Lys Tyr
         1               5                  10                 15
         Trp Gly Lys Lys Asp Ala Lys Leu Arg Leu Pro Leu Met Ser Ser Leu
                         20                 25                 30
         Ser Met Thr Leu Asp Ala Phe Tyr Ser Asp Thr Lys Ile Ser Asp Ser
                         35                 40                 45
```

```
Glu Gln Met Ser Phe Lys Leu Asn Gly Gln Ala Val Ser Gly Pro Ala
        50                  55                  60

Ala Asp Arg Val Phe Ala Tyr Leu Arg Ala Met Gln Asp Arg Phe Gly
 65                  70                  75                  80

Val Lys Gly Asn Leu Ala Val Glu Ser Val Asn Gln Val Pro Thr Ala
                    85                  90                  95

Ala Gly Leu Ala Ser Ser Ser Ala Phe Ala Met Ala Ala Ala
                100                 105                 110

Phe Ala Asp His Tyr Gln Leu Gly Val Asp Arg Gln Glu Leu Ser Arg
                115                 120                 125

Met Ala Arg Met Gly Ser Gly Ser Ala Ser Arg Ser Val Phe Gly Gly
        130                 135                 140

Phe Ser Val Trp Gln Lys Gly Asp Ser Asp Gln Thr Ser Tyr Ala Tyr
145                 150                 155                 160

Pro Leu Asp Glu Glu Pro Asp Met Asp Leu Arg Leu Leu Ala Val Glu
                165                 170                 175

Ile Asn Asp Gln Glu Lys Lys Ile Ser Ser Thr Lys Gly Met Glu Met
                180                 185                 190

Ser Lys Ser Ser Pro Phe Tyr Gln Val Trp Leu Asp Arg Asn Asp Ser
        195                 200                 205

Glu Ile Lys Glu Met Glu Glu Ala Ile Lys Gln Ala Asp Phe Ser Lys
210                 215                 220

Leu Gly Ser Leu Ala Glu Leu Asn Ala Ser Glu Met His Thr Leu Thr
225                 230                 235                 240

Phe Thr Ala Val Pro Gly Phe Thr Tyr Phe Glu Pro Asn Thr Ile Lys
                245                 250                 255

Ala Ile Lys Leu Val Gln Asp Leu Arg Gln Gln Gly Leu Glu Cys Tyr
                260                 265                 270

Tyr Thr Ile Asp Ala Gly Pro Asn Val Lys Val Leu Cys Gln Gly Lys
        275                 280                 285

Asn Ser Lys Asp Ile Ile Asn Cys Phe Glu Ser Ser Phe Asp Arg Val
        290                 295                 300

Lys Ile Ile Glu Ala Gly Phe Gly Pro Gly Val Thr Leu Leu Asp
305                 310                 315

<210> SEQ ID NO 8
<211> LENGTH: 324
<212> TYPE: PRT
<213> ORGANISM: Haloquadratum walsbyi

<400> SEQUENCE: 8

Met Lys Ala Thr Ala Arg Ala His Pro Ile Gln Gly Leu Ile Lys Tyr
 1               5                  10                  15

His Gly Met Arg Asp Ser Asp Lys Arg Tyr Pro Tyr His Asp Ser Ile
                20                  25                  30

Ser Val Cys Thr Ala Pro Ser Ala Thr Thr Thr Val Glu Phe Gln
        35                  40                  45

Ser Asp Ala Ser Gly Asp Val Tyr Ile Ile Asp Asn Glu Arg Val Asp
 50                  55                  60

Gly Arg Ala Ala Glu Arg Ile Asp Ala Val Val Glu His Val Arg Glu
 65                  70                  75                  80

Arg Thr Gly Ile Arg Asp Pro Val Arg Leu Val Ser Thr Asn Ser Phe
                    85                  90                  95

Pro Ser Asn Ile Gly Phe Gly Ser Ser Ser Ser Gly Phe Ala Ala Ala
```

-continued

```
                100                 105                 110
Ala Met Ala Leu Val Thr Ala Ala Gly Glu Glu Leu Thr His Pro Glu
            115                 120                 125

Ile Ser Thr Ile Ala Arg Arg Gly Ser Ser Ala Ala Arg Ala Val
        130                 135                 140

Thr Gly Ala Phe Ser Gln Leu Tyr Ser Gly Met Asn Asp Thr Asp Cys
145                 150                 155                 160

His Ala Glu Arg Ile Glu Thr Asp Leu Asp Ala Thr Val Arg Thr Val
                165                 170                 175

Ala Ala His Val Pro Ala Tyr Lys Glu Thr Glu Glu Ala His Arg Glu
            180                 185                 190

Ala Ala Gln Ser His Met Phe Asp Ala Arg Leu Ala His Val His His
        195                 200                 205

Gln Ile Asp Ala Met Arg Asp Ala Leu Tyr Asn Ala Asp Phe Asp Arg
    210                 215                 220

Ile Phe Glu Leu Ala Glu His Asp Ser Leu Ser Leu Thr Ala Ala Thr
225                 230                 235                 240

Met Thr Gly Pro Ala Gly Trp Val Tyr Trp Gln Pro Gln Thr Ile Ala
                245                 250                 255

Val Phe Asn Thr Val Arg Glu Leu Arg Glu Arg Glu Ser Ile Pro Val
            260                 265                 270

Tyr Phe Ser Thr Asp Thr Gly Ala Ser Val Tyr Val Asn Thr Thr Ala
        275                 280                 285

Ala His Val Asp Thr Val Glu Ser Ala Ile Ser Asp Ile Gly Ile Asp
    290                 295                 300

Thr Asp Ile Trp Thr Val Gly Gly Pro Ala Thr Val Leu Ser Ala Ser
305                 310                 315                 320

Asp Ser Leu Phe

<210> SEQ ID NO 9
<211> LENGTH: 322
<212> TYPE: PRT
<213> ORGANISM: Lactobacillus salivarius
<221> NAME/KEY:
<223> OTHER INFORMATION: /sub-species = salivarius

<400> SEQUENCE: 9

Met Ser Asn His Ala Ala Arg Ala His Thr Asn Ile Ala Leu Ile
1               5                   10                  15

Lys Tyr Trp Gly Lys Lys Asp Thr Glu Leu Ile Leu Pro Met Asn Asn
            20                  25                  30

Ser Leu Ser Leu Thr Leu Asp His Phe Tyr Thr Asp Thr Ser Val Thr
        35                  40                  45

Phe Asp Ser Ser Tyr Thr Lys Asp Thr Phe Ile Leu Asn Gly Lys Glu
    50                  55                  60

Ile Pro Asn Glu Asn Val His Lys Phe Leu Asn Ile Val Arg Glu Lys
65                  70                  75                  80

Ala Gly Ile Ser Glu Phe Ala Lys Val Asn Ser Thr Asn His Val Pro
                85                  90                  95

Thr Thr Ala Gly Leu Ala Ser Ser Ala Ser Ala Phe Ala Ala Leu Ala
            100                 105                 110

Ala Ala Ala Ser Lys Ala Ser Gly Met Asn Leu Ser Arg Arg Asp Leu
        115                 120                 125

Ser Arg Leu Ala Arg Arg Gly Ser Gly Ser Ala Thr Arg Ser Ile Tyr
    130                 135                 140
```

```
Gly Gly Phe Val Glu Trp Gln Ala Gly Asp Asn Asp Leu Asn Ser Tyr
145                 150                 155                 160

Ala Val Pro Phe Ile Glu Asn Val Ser Trp Asp Ile Lys Met Ile Ala
                165                 170                 175

Val Val Ile Asn Ser Lys Pro Lys Lys Ile Thr Ser Arg Ala Gly Met
            180                 185                 190

Gln Thr Val Val Asn Thr Ser Pro Tyr Tyr Asn Ser Trp Ile Lys Glu
        195                 200                 205

Ala Asn Arg Ser Ile Pro Leu Met Lys Glu Ala Ile Ser Lys Gln Asp
    210                 215                 220

Phe Thr Thr Met Gly Glu Leu Ala Glu Asn Ala Met Lys Met His
225                 230                 235                 240

Ala Leu Asn Leu Ser Ala His Pro His Phe Ser Tyr Phe Ser Pro Glu
                245                 250                 255

Ser Ile Gln Val Met Asn Leu Val Glu Glu Leu Arg Ser Met Gly Ile
            260                 265                 270

Glu Cys Tyr Tyr Thr Met Asp Ala Gly Pro Asn Val Lys Ile Ile Cys
        275                 280                 285

Leu Gly Lys Asp Thr Ala Ser Ile Thr Ser Phe Leu Gln Lys Asn Leu
    290                 295                 300

Pro Asn Thr Glu Val Leu Val Ser Ser Ala Gly Pro Gly Val Gln Tyr
305                 310                 315                 320

Leu Asp

<210> SEQ ID NO 10
<211> LENGTH: 314
<212> TYPE: PRT
<213> ORGANISM: Oenococcus oeni

<400> SEQUENCE: 10

Met Ala Lys Val Arg Ala Tyr Thr Asn Ile Ala Leu Ile Lys Tyr Trp
1               5                   10                  15

Gly Lys Ser Asp Leu Asn Trp Asn Leu Pro Thr Ser Ser Ile Gly
            20                  25                  30

Leu Thr Leu Asp Arg Phe Tyr Thr Asp Thr Ser Val Glu Ile Asp Gln
        35                  40                  45

Phe Ser Lys Lys Asp Phe Phe Gln Leu Asn Gly Gln Gln Ile Glu Gly
    50                  55                  60

Pro Lys Ile Ser Lys Ile Ile Asn Phe Ile Arg Asn Ser Cys Gly Asn
65                  70                  75                  80

Lys Asn Phe Val Lys Val Ile Ser Glu Asn His Val Pro Thr Ser Ala
                85                  90                  95

Gly Leu Ala Ser Ser Ala Ser Ala Phe Ala Ala Leu Thr Lys Ala Ala
            100                 105                 110

Asn Gln Ala Phe Gly Leu Glu Leu Asp Asn Arg Glu Leu Ser Lys Ile
        115                 120                 125

Ala Arg Ile Gly Ser Gly Ser Ala Ser Arg Ser Ile Phe Gly Gly Phe
    130                 135                 140

Ser Ile Trp His Lys Gly Gln Asn Lys Asp Asp Ser Phe Ala Glu Ser
145                 150                 155                 160

Ile Leu Asp Pro Val Asp Phe Asp Ile Arg Val Ile Asp Ile Leu Ala
                165                 170                 175

Asp Lys Arg Val Lys Lys Ile Ser Ser Ser Gln Gly Met Gln Leu Ala
            180                 185                 190
```

```
Gln Thr Ser Pro Asn Tyr Asp Ser Trp Leu Lys Lys Asn Asp Arg Gln
            195                 200                 205

Ile Asp Glu Met Leu Lys Ala Ile Ser Asp His Asp Leu Glu Lys Ile
210                 215                 220

Gly Leu Ile Ala Glu Thr Asn Ser Ala Ser Met His Glu Leu Asn Arg
225                 230                 235                 240

Thr Ala Lys Val Pro Phe Asp Tyr Phe Thr Glu Asn Thr Arg Glu Ile
            245                 250                 255

Ile Ala Glu Val Asp Gln Leu Tyr Lys Lys Gly Ile Leu Ala Phe Ala
            260                 265                 270

Thr Val Asp Ala Gly Pro Asn Val Lys Val Ile Thr Asn Ser Glu Tyr
            275                 280                 285

Gln Glu Lys Ile Ile Asn Val Leu Lys Glu Tyr Gly Glu Ile Leu Val
            290                 295                 300

Gln Lys Pro Gly Arg Gly Val Ala Asn Val
305                 310

<210> SEQ ID NO 11
<211> LENGTH: 327
<212> TYPE: PRT
<213> ORGANISM: Pediococcus pentosaceus

<400> SEQUENCE: 11

Met Asn Glu Lys His Gly Phe Ala Arg Ala His Thr Asn Ile Ala Leu
1               5                   10                  15

Leu Lys Tyr Trp Gly Lys Ile Asn Ser Asp Leu Ile Leu Pro Ala Asn
            20                  25                  30

Asp Ser Ile Ser Leu Thr Leu Asp Lys Phe Tyr Thr Asp Thr Glu Val
        35                  40                  45

Thr Phe Ser Asp Glu Tyr Thr Ser Asn Leu Phe Tyr Leu Asn His Gln
    50                  55                  60

Leu Ile Asp Val Lys Lys Met Gln Arg Ile Asn Arg Val Leu Glu Ala
65                  70                  75                  80

Val Lys Ser Glu Phe Gly Tyr Gln Gly Phe Ala Lys Ile Glu Ser Glu
                85                  90                  95

Asn His Val Pro Thr Ala Ala Gly Leu Ala Ser Ser Ala Ser Gly Met
            100                 105                 110

Ala Ala Leu Ala Gly Ala Ala Val Ser Ala Leu Gly Ser His Thr Asp
        115                 120                 125

Leu Thr Asn Leu Ser Arg Leu Ala Arg Leu Gly Ser Gly Ser Ala Ser
    130                 135                 140

Arg Ser Val Phe Gly Gly Ile Val His Trp His Arg Gly Tyr Asp His
145                 150                 155                 160

Gln Ser Ser Phe Ala Glu Gln Ile Val Ser Glu Asp Gln Ile Asp Leu
                165                 170                 175

Asn Met Val Thr Ile Val Ile Asp Arg Arg Gln Lys Lys Val Lys Ser
            180                 185                 190

Thr Leu Gly Met Gln His Thr Ala Ser Thr Ser Pro Phe Tyr Pro Ala
        195                 200                 205

Trp Val Glu Ala Thr Asn Gln Ala Ile Pro Glu Met Ile Ser Ala Val
    210                 215                 220

Gln Asn Asn Asp Phe Thr Lys Ile Gly Glu Leu Ala Glu His Ser Ala
225                 230                 235                 240

Ala Met Met His Ala Thr Thr Leu Ser Ser Lys Pro Ala Phe Thr Tyr
```

```
                        245                 250                 255
Phe Ala Pro Glu Thr Ile Gln Ala Ile Lys Leu Val Glu Gln Leu Arg
            260                 265                 270

Glu Ser Gly Ile Glu Cys Tyr Tyr Thr Ile Asp Ala Gly Pro Asn Val
        275                 280                 285

Lys Val Leu Cys Gln Ser Lys Asn Ile Thr Arg Val Lys Arg Phe Phe
    290                 295                 300

Ala Ser Tyr Phe Asp Gln Asp Gln Leu Val Val Ala Lys Pro Gly Ser
305                 310                 315                 320

Gly Ile Lys Phe Thr Lys Asn
                325

<210> SEQ ID NO 12
<211> LENGTH: 315
<212> TYPE: PRT
<213> ORGANISM: Streptococcus gordonii

<400> SEQUENCE: 12

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Glu Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Gln Ala Met Leu Gly Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285
```

Asp Leu Asp His Leu Ala Ala Ile Phe Glu Lys Asp Tyr Arg Leu Ile
290                 295                 300

Val Ser Lys Thr Lys Asp Leu Ser Asp Glu Ser
305                 310                 315

<210> SEQ ID NO 13
<211> LENGTH: 328
<212> TYPE: PRT
<213> ORGANISM: Dichelobacter nodosus

<400> SEQUENCE: 13

Met His Ser Ala Thr Ala Phe Ala Pro Ala Asn Ile Ala Leu Ala Lys
1               5                   10                  15

Tyr Trp Gly Lys Arg Asp Ala Gln Leu Asn Leu Pro Thr Asn Gly Ser
                20                  25                  30

Leu Ser Ile Ser Leu Ala His Leu Gly Thr Thr Thr Ile Ser Ala
            35                  40                  45

Gly Glu Arg Asp Gln Leu Tyr Cys Asp His Arg Leu Leu Pro Pro Asp
        50                  55                  60

Thr Ala Phe Val Gln Lys Val Trp His Phe Ile Asp Phe Cys Gln Pro
65                  70                  75                  80

Lys Arg Pro Pro Leu Val Ile His Thr Gln Asn Asn Ile Pro Thr Ala
                85                  90                  95

Ala Gly Leu Ala Ser Ser Ala Ser Gly Phe Ala Ala Leu Thr Leu Ala
            100                 105                 110

Leu Asn Asp Phe Phe Gln Trp Ser Leu Ser Arg Glu Gln Leu Ser Gln
        115                 120                 125

Ile Ala Arg Arg Gly Ser Gly Ser Ala Cys Arg Ser Leu Trp Gln Gly
    130                 135                 140

Phe Val Tyr Trp Gln Lys Gly Glu Lys Ala Asp Gly Ser Asp Cys Tyr
145                 150                 155                 160

Ala Arg Pro Ile Ala Ser Asp Trp Gln Asp Leu Arg Leu Gly Ile Ile
                165                 170                 175

Thr Ile Asp Ala Ala Lys Lys Ile Ser Ser Arg Gln Ala Met Asn
            180                 185                 190

His Thr Ala Ala Ser Ser Pro Leu Phe Ser Ser Trp Thr Gln Ala Ala
        195                 200                 205

Glu Ala Asp Leu Lys Val Ile Tyr Gln Ala Val Leu Asp Arg Asp Phe
    210                 215                 220

Leu Thr Leu Ala Gln Thr Ala Glu Ala Asn Ala Leu Met Met His Ala
225                 230                 235                 240

Ser Leu Leu Ala Ala Arg Pro Ala Ile Phe Tyr Trp Gln Pro Gln Thr
                245                 250                 255

Leu Ala Met Leu Gln Cys Ile Trp Gln Ala Arg Ala Glu Gly Leu Ala
            260                 265                 270

Val Tyr Ala Thr Leu Asp Ala Gly Ala Asn Val Lys Leu Leu Tyr Arg
        275                 280                 285

Ala Gln Asp Glu Ala Glu Ile Ala Ser Met Phe Pro Gln Ala Gln Leu
    290                 295                 300

Ile Asn Pro Phe Gln Thr Val Thr Ser Ser Ala Arg His Thr Gly Glu
305                 310                 315                 320

Asp Ala Gln Lys Pro Ser Leu Lys
                325

<210> SEQ ID NO 14

<211> LENGTH: 317
<212> TYPE: PRT
<213> ORGANISM: Streptococcus pneumoniae

<400> SEQUENCE: 14

```
Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Ala Asn Val Thr Ala Asp Glu Phe Tyr Ile Asn Gly
50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315
```

<210> SEQ ID NO 15
<211> LENGTH: 314
<212> TYPE: PRT
<213> ORGANISM: Streptococcus pyogenes

<400> SEQUENCE: 15

```
Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30
```

Ser Ser Ile Ser Leu Thr Leu Glu Asn Met Phe Thr Thr Thr Ser Val
           35                  40                  45

Ser Phe Leu Pro Asp Thr Ala Thr Ser Asp Gln Phe Tyr Ile Asn Gly
 50                  55                  60

Val Leu Gln Asn Asp Glu Glu His Thr Lys Ile Ser Ala Ile Ile Asp
 65                  70                  75                  80

Gln Phe Arg Gln Pro Gly Gln Ala Phe Val Lys Met Glu Thr Gln Asn
                 85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asn Thr Gln Leu Asp Gln
            115                 120                 125

Lys Ala Leu Ala Gln Lys Ala Lys Phe Ala Ser Gly Ser Ser Ser Arg
            130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Glu Trp Val Glu Gln Ser Ala Ile
            195                 200                 205

Asp Tyr Gln His Met Leu Thr Tyr Leu Lys Thr Asn Asn Phe Glu Lys
            210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
            260                 265                 270

Phe Thr Met Asp Ala Gly Pro Asn Val Lys Val Leu Cys Leu Glu Lys
            275                 280                 285

Asp Leu Ala Gln Leu Ala Glu Arg Leu Gly Lys Asn Tyr Arg Ile Ile
            290                 295                 300

Val Ser Lys Thr Lys Asp Leu Pro Asp Val
305                 310

<210> SEQ ID NO 16
<211> LENGTH: 320
<212> TYPE: PRT
<213> ORGANISM: Lactobacillus acidophilus NCFM

<400> SEQUENCE: 16

Met Lys Asn Thr Ala Arg Ala His Thr Asn Ile Ala Leu Ile Lys Tyr
1                5                  10                  15

Trp Gly Lys Ser Asp Pro Ile Leu Arg Leu Pro Leu Met Ser Ser Leu
                20                  25                  30

Ser Met Thr Leu Asp Ala Phe Tyr Thr Asp Thr Leu Ile Glu Lys Thr
            35                  40                  45

Asp Ala Lys Asn Glu Phe Tyr Leu Asn Gly Lys Arg Gln Asn Arg Gln
         50                  55                  60

Ala Lys Lys Arg Val Phe Ser Tyr Leu Asp Thr Leu Lys Glu Lys Phe
65                  70                  75                  80

Gly Tyr Thr Asp Asn Leu Ile Val Lys Ser Thr Asn His Val Pro Thr

```
                    85                  90                  95
Ser Ala Gly Leu Ala Ser Ser Ser Ala Phe Ala Ala Leu Ala Ala
                100                 105                 110

Ser Phe Cys Lys Leu Tyr Asn Leu Asp Val Asp Lys Thr Glu Leu Ser
                115                 120                 125

Arg Leu Ala Arg Leu Gly Ser Gly Ala Ser Arg Ser Ile Phe Gly
            130                 135                 140

Gly Phe Ala Ile Trp Gln Lys Gly Asn Ser Asn Gln Ser Ser Tyr Ala
145                 150                 155                 160

Tyr Ala Leu Asp Glu Lys Pro Lys Met Asp Leu Gln Leu Leu Ala Val
                165                 170                 175

Glu Leu Asn Thr Glu Gln Lys Lys Ile Ser Ser Thr Lys Gly Met Lys
            180                 185                 190

Asp Ala Gln Ser Ser Pro Phe Phe Ser Thr Trp Thr Asn Arg Asn Gln
                195                 200                 205

Leu Glu Leu Asp Glu Met Ile Lys Ala Ile Lys Gln Asn Asp Phe Thr
            210                 215                 220

Ala Leu Gly Ser Leu Ala Glu Leu Asn Ala Asn Glu Met His Ala Ile
225                 230                 235                 240

Asn Leu Thr Ala Gln Pro Glu Phe Thr Tyr Phe Met Pro Glu Thr Ile
                245                 250                 255

Arg Ala Ile Lys Leu Val Glu Asp Leu Arg Thr Lys Gly Ile Glu Cys
            260                 265                 270

Tyr Tyr Thr Ile Asp Ala Gly Pro Asn Ile Lys Val Leu Cys Gln Leu
        275                 280                 285

Lys Asn Arg Lys Glu Ile Ile Glu His Phe Glu Ser Val Phe Asn Asn
            290                 295                 300

Val Asn Ile Val Ser Ala Ser Phe Gly Pro Gly Val Ile Tyr Leu Asp
305                 310                 315                 320
```

<210> SEQ ID NO 17
<211> LENGTH: 996
<212> TYPE: DNA
<213> ORGANISM: artificial sequence
<220> FEATURE:
<221> NAME/KEY: Source
<223> OTHER INFORMATION: /note=?Description of Artificial Sequence:
    Optimized sequence of P. torridus (AAT43941) MDP decarboxylase
    including the His Tag)?
<220> FEATURE:
<221> NAME/KEY: CDS
<222> LOCATION: (1)..(996)

<400> SEQUENCE: 17

```
atg cat cat cat cat cac cac gag aac tat aat gtt aaa acc cgt gca    48
Met His His His His His His Glu Asn Tyr Asn Val Lys Thr Arg Ala
1               5                   10                  15 ttt ccg acc att ggt att att ctg ctg ggt ggc att agc gac aaa aaa    96
Phe Pro Thr Ile Gly Ile Ile Leu Leu Gly Gly Ile Ser Asp Lys Lys
            20                  25                  30 aac cgt att ccg ctg cat acc acc gca ggt att gca tat acc ggc atc   144
Asn Arg Ile Pro Leu His Thr Thr Ala Gly Ile Ala Tyr Thr Gly Ile
        35                  40                  45 aat aac gat gtg tac acc gaa acc aaa ctg tat gtg agc aaa gac gaa   192
Asn Asn Asp Val Tyr Thr Glu Thr Lys Leu Tyr Val Ser Lys Asp Glu
 50                  55                  60 aaa tgc tat atc gat ggc aaa gaa atc gat ctg aat agc gat cgt agc   240
Lys Cys Tyr Ile Asp Gly Lys Glu Ile Asp Leu Asn Ser Asp Arg Ser
65                  70                  75                  80
```

```
ccg agc aaa gtg atc gat aaa ttc aaa cat gaa atc ctg atg cgt gtg      288
Pro Ser Lys Val Ile Asp Lys Phe Lys His Glu Ile Leu Met Arg Val
                 85                  90                  95 aat ctg gat gat gaa aac aac ctg agc att gat agc cgc aat ttt aac      336
Asn Leu Asp Asp Glu Asn Asn Leu Ser Ile Asp Ser Arg Asn Phe Asn
            100                 105                 110 att ctg agc ggt agc agc gat agc ggt gca gca gca ctg ggt gaa tgc      384
Ile Leu Ser Gly Ser Ser Asp Ser Gly Ala Ala Ala Leu Gly Glu Cys
        115                 120                 125 att gaa agc atc ttc gag tac aac atc aac atc ttc acc ttt gaa aat      432
Ile Glu Ser Ile Phe Glu Tyr Asn Ile Asn Ile Phe Thr Phe Glu Asn
    130                 135                 140 gat ctg cag cgt att agc gaa agc gtt ggt cgt agc ctg tat ggt ggt      480
Asp Leu Gln Arg Ile Ser Glu Ser Val Gly Arg Ser Leu Tyr Gly Gly
145                 150                 155                 160 ctg acc gtt aat tat gca aat ggt cgt gaa agc ctg acc gaa ccg ctg      528
Leu Thr Val Asn Tyr Ala Asn Gly Arg Glu Ser Leu Thr Glu Pro Leu
                165                 170                 175 ctg gaa ccg gaa gca ttt aac aac ttt acc atc atc ggt gcc cat ttt      576
Leu Glu Pro Glu Ala Phe Asn Asn Phe Thr Ile Ile Gly Ala His Phe
            180                 185                 190 aac att gat cgc aaa ccg agc aac gaa atc cac gaa aac atc atc aaa      624
Asn Ile Asp Arg Lys Pro Ser Asn Glu Ile His Glu Asn Ile Ile Lys
        195                 200                 205 cat gag aac tat cgc gaa cgt att aaa agc gca gag cgc aaa gca aaa      672
His Glu Asn Tyr Arg Glu Arg Ile Lys Ser Ala Glu Arg Lys Ala Lys
    210                 215                 220 aaa ctg gaa gaa ctg agc cgt aat gcc aac att aaa ggc att ttt gaa      720
Lys Leu Glu Glu Leu Ser Arg Asn Ala Asn Ile Lys Gly Ile Phe Glu
225                 230                 235                 240 ctg gca gaa agc gat acc gtg gaa tat cat aaa atg ctg cat gat gtg      768
Leu Ala Glu Ser Asp Thr Val Glu Tyr His Lys Met Leu His Asp Val
                245                 250                 255 ggc gtt gat att atc aat gac cgc atg gaa aat ctg att gaa cgc gtg      816
Gly Val Asp Ile Ile Asn Asp Arg Met Glu Asn Leu Ile Glu Arg Val
            260                 265                 270 aaa gag atg aaa aac aac ttc tgg aac agc tat att gtt acc ggt ggt      864
Lys Glu Met Lys Asn Asn Phe Trp Asn Ser Tyr Ile Val Thr Gly Gly
        275                 280                 285 ccg aat gtt ttt gtg atc acc gag aaa aaa gat gtg gat aaa gcc atg      912
Pro Asn Val Phe Val Ile Thr Glu Lys Lys Asp Val Asp Lys Ala Met
    290                 295                 300 gaa ggt ctg aat gat ctg tgt gat gat att cgt ctg ctg aaa gtt gca      960
Glu Gly Leu Asn Asp Leu Cys Asp Asp Ile Arg Leu Leu Lys Val Ala
305                 310                 315                 320 ggt aaa ccg cag gtt atc agc aaa aac ttc taa tga                      996
Gly Lys Pro Gln Val Ile Ser Lys Asn Phe
                325                 330
```

<210> SEQ ID NO 18
<211> LENGTH: 330
<212> TYPE: PRT
<213> ORGANISM: artificial sequence
<220> FEATURE:
<223> OTHER INFORMATION: Synthetic Construct

<400> SEQUENCE: 18

```
Met His His His His His Glu Asn Tyr Asn Val Lys Thr Arg Ala
1               5                   10                  15

Phe Pro Thr Ile Gly Ile Ile Leu Leu Gly Gly Ile Ser Asp Lys Lys
```

```
            20                  25                  30
Asn Arg Ile Pro Leu His Thr Thr Ala Gly Ile Ala Tyr Thr Gly Ile
            35                  40                  45

Asn Asn Asp Val Tyr Thr Glu Thr Lys Leu Tyr Val Ser Lys Asp Glu
        50                  55                  60

Lys Cys Tyr Ile Asp Gly Lys Glu Ile Asp Leu Asn Ser Asp Arg Ser
65                  70                  75                  80

Pro Ser Lys Val Ile Asp Lys Phe Lys His Glu Ile Leu Met Arg Val
                85                  90                  95

Asn Leu Asp Asp Glu Asn Asn Leu Ser Ile Asp Ser Arg Asn Phe Asn
            100                 105                 110

Ile Leu Ser Gly Ser Ser Asp Ser Gly Ala Ala Ala Leu Gly Glu Cys
        115                 120                 125

Ile Glu Ser Ile Phe Glu Tyr Asn Ile Asn Ile Phe Thr Phe Glu Asn
    130                 135                 140

Asp Leu Gln Arg Ile Ser Glu Ser Val Gly Arg Ser Leu Tyr Gly Gly
145                 150                 155                 160

Leu Thr Val Asn Tyr Ala Asn Gly Arg Glu Ser Leu Thr Glu Pro Leu
                165                 170                 175

Leu Glu Pro Glu Ala Phe Asn Asn Phe Thr Ile Ile Gly Ala His Phe
            180                 185                 190

Asn Ile Asp Arg Lys Pro Ser Asn Glu Ile His Glu Asn Ile Ile Lys
        195                 200                 205

His Glu Asn Tyr Arg Glu Arg Ile Lys Ser Ala Glu Arg Lys Ala Lys
    210                 215                 220

Lys Leu Glu Glu Leu Ser Arg Asn Ala Asn Ile Lys Gly Ile Phe Glu
225                 230                 235                 240

Leu Ala Glu Ser Asp Thr Val Glu Tyr His Lys Met Leu His Asp Val
                245                 250                 255

Gly Val Asp Ile Ile Asn Asp Arg Met Glu Asn Leu Ile Glu Arg Val
            260                 265                 270

Lys Glu Met Lys Asn Asn Phe Trp Asn Ser Tyr Ile Val Thr Gly Gly
        275                 280                 285

Pro Asn Val Phe Val Ile Thr Glu Lys Lys Asp Val Asp Lys Ala Met
    290                 295                 300

Glu Gly Leu Asn Asp Leu Cys Asp Asp Ile Arg Leu Leu Lys Val Ala
305                 310                 315                 320

Gly Lys Pro Gln Val Ile Ser Lys Asn Phe
                325                 330
```

<210> SEQ ID NO 19
<211> LENGTH: 993
<212> TYPE: DNA
<213> ORGANISM: Artificial sequence
<220> FEATURE:
<221> NAME/KEY: Source
<223> OTHER INFORMATION: /note=?Description of Artificial Sequence:
      Native sequence of P. torridus (AAT43941) MDP decarboxylase
      including the His Tag)?
<220> FEATURE:
<221> NAME/KEY: CDS
<222> LOCATION: (1)..(993)

<400> SEQUENCE: 19

```
atg cat cat cac cat cac cat gaa aat tac aat gtt aag aca agg gcg      48
Met His His His His His His Glu Asn Tyr Asn Val Lys Thr Arg Ala
1               5                   10                  15
```

```
ttc cca aca ata ggc ata ata ctg ctt ggt ggg atc tcg gat aaa aag      96
Phe Pro Thr Ile Gly Ile Ile Leu Leu Gly Gly Ile Ser Asp Lys Lys
             20                  25                  30 aac agg ata ccg ctg cat aca acg gca ggc ata gca tat act ggt ata     144
Asn Arg Ile Pro Leu His Thr Thr Ala Gly Ile Ala Tyr Thr Gly Ile
         35                  40                  45 aac aat gat gtt tac act gag aca aag ctt tat gta tca aaa gat gaa     192
Asn Asn Asp Val Tyr Thr Glu Thr Lys Leu Tyr Val Ser Lys Asp Glu
 50                  55                  60 aaa tgc tat att gat gga aag gaa att gat tta aat tca gat aga tca     240
Lys Cys Tyr Ile Asp Gly Lys Glu Ile Asp Leu Asn Ser Asp Arg Ser
 65                  70                  75                  80 cca tcg aag gtt att gat aaa ttc aag cat gaa ata ctt atg aga gta     288
Pro Ser Lys Val Ile Asp Lys Phe Lys His Glu Ile Leu Met Arg Val
             85                  90                  95 aat ctt gat gat gaa aat aac ctt tca att gat tca agg aac ttt aat     336
Asn Leu Asp Asp Glu Asn Asn Leu Ser Ile Asp Ser Arg Asn Phe Asn
            100                 105                 110 ata tta agt ggc agc tca gat tct ggg gcc gct gca ctg gga gag tgc     384
Ile Leu Ser Gly Ser Ser Asp Ser Gly Ala Ala Ala Leu Gly Glu Cys
            115                 120                 125 ata gaa tca att ttt gaa tac aat ata aat ata ttt aca ttt gaa aac     432
Ile Glu Ser Ile Phe Glu Tyr Asn Ile Asn Ile Phe Thr Phe Glu Asn
130                 135                 140 gat ctt cag agg ata tca gaa agt gtt gga aga agc ctt tac ggt ggt     480
Asp Leu Gln Arg Ile Ser Glu Ser Val Gly Arg Ser Leu Tyr Gly Gly
145                 150                 155                 160 tta aca gta aac tat gcc aat ggc agg gaa tca tta aca gag cca tta     528
Leu Thr Val Asn Tyr Ala Asn Gly Arg Glu Ser Leu Thr Glu Pro Leu
                165                 170                 175 ctt gag cct gag gca ttt aat aac ttt aca ata att ggt gca cat ttt     576
Leu Glu Pro Glu Ala Phe Asn Asn Phe Thr Ile Ile Gly Ala His Phe
            180                 185                 190 aac att gat aga aaa cca tca aat gag att cat gaa aat atc ata aaa     624
Asn Ile Asp Arg Lys Pro Ser Asn Glu Ile His Glu Asn Ile Ile Lys
        195                 200                 205 cat gaa aat tac agg gaa aga ata aaa agt gct gag aga aag gcg aaa     672
His Glu Asn Tyr Arg Glu Arg Ile Lys Ser Ala Glu Arg Lys Ala Lys
210                 215                 220 aaa ctt gag gag cta tca agg aat gca aac ata aag ggt atc ttt gaa     720
Lys Leu Glu Glu Leu Ser Arg Asn Ala Asn Ile Lys Gly Ile Phe Glu
225                 230                 235                 240 ctt gca gaa tcc gat aca gtg gaa tac cat aaa atg ctc cat gat gtt     768
Leu Ala Glu Ser Asp Thr Val Glu Tyr His Lys Met Leu His Asp Val
                245                 250                 255 ggc gtt gac ata ata aat gat aga atg gag aac ctc att gaa agg gta     816
Gly Val Asp Ile Ile Asn Asp Arg Met Glu Asn Leu Ile Glu Arg Val
            260                 265                 270 aaa gaa atg aaa aat aac ttc tgg aat tca tac ata gtt acc ggc ggc     864
Lys Glu Met Lys Asn Asn Phe Trp Asn Ser Tyr Ile Val Thr Gly Gly
        275                 280                 285 ccg aac gtt ttt gta ata aca gag aaa aag gac gtt gat aag gca atg     912
Pro Asn Val Phe Val Ile Thr Glu Lys Lys Asp Val Asp Lys Ala Met
290                 295                 300 gaa gga tta aat gat ctg tgc gat gat ata aga tta tta aaa gtt gca     960
Glu Gly Leu Asn Asp Leu Cys Asp Asp Ile Arg Leu Leu Lys Val Ala
305                 310                 315                 320 gga aag cca cag gtc att tca aaa aac ttt taa                         993
Gly Lys Pro Gln Val Ile Ser Lys Asn Phe
                325                 330
```

<210> SEQ ID NO 20
<211> LENGTH: 330
<212> TYPE: PRT
<213> ORGANISM: Artificial sequence
<220> FEATURE:
<223> OTHER INFORMATION: Synthetic Construct

<400> SEQUENCE: 20

Met His His His His His Glu Asn Tyr Asn Val Lys Thr Arg Ala
1               5                   10                  15

Phe Pro Thr Ile Gly Ile Ile Leu Leu Gly Gly Ile Ser Asp Lys Lys
                20                  25                  30

Asn Arg Ile Pro Leu His Thr Thr Ala Gly Ile Ala Tyr Thr Gly Ile
            35                  40                  45

Asn Asn Asp Val Tyr Thr Glu Thr Lys Leu Tyr Val Ser Lys Asp Glu
50                  55                  60

Lys Cys Tyr Ile Asp Gly Lys Glu Ile Asp Leu Asn Ser Asp Arg Ser
65                  70                  75                  80

Pro Ser Lys Val Ile Asp Lys Phe Lys His Glu Ile Leu Met Arg Val
                85                  90                  95

Asn Leu Asp Asp Glu Asn Asn Leu Ser Ile Asp Ser Arg Asn Phe Asn
            100                 105                 110

Ile Leu Ser Gly Ser Ser Asp Ser Gly Ala Ala Ala Leu Gly Glu Cys
            115                 120                 125

Ile Glu Ser Ile Phe Glu Tyr Asn Ile Asn Ile Phe Thr Phe Glu Asn
            130                 135                 140

Asp Leu Gln Arg Ile Ser Glu Ser Val Gly Arg Ser Leu Tyr Gly Gly
145                 150                 155                 160

Leu Thr Val Asn Tyr Ala Asn Gly Arg Glu Ser Leu Thr Glu Pro Leu
                165                 170                 175

Leu Glu Pro Glu Ala Phe Asn Asn Phe Thr Ile Ile Gly Ala His Phe
            180                 185                 190

Asn Ile Asp Arg Lys Pro Ser Asn Glu Ile His Glu Asn Ile Ile Lys
            195                 200                 205

His Glu Asn Tyr Arg Glu Arg Ile Lys Ser Ala Glu Arg Lys Ala Lys
        210                 215                 220

Lys Leu Glu Glu Leu Ser Arg Asn Ala Asn Ile Lys Gly Ile Phe Glu
225                 230                 235                 240

Leu Ala Glu Ser Asp Thr Val Glu Tyr His Lys Met Leu His Asp Val
                245                 250                 255

Gly Val Asp Ile Ile Asn Asp Arg Met Glu Asn Leu Ile Glu Arg Val
            260                 265                 270

Lys Glu Met Lys Asn Asn Phe Trp Asn Ser Tyr Ile Val Thr Gly Gly
            275                 280                 285

Pro Asn Val Phe Val Ile Thr Glu Lys Asp Val Asp Lys Ala Met
            290                 295                 300

Glu Gly Leu Asn Asp Leu Cys Asp Asp Ile Arg Leu Leu Lys Val Ala
305                 310                 315                 320

Gly Lys Pro Gln Val Ile Ser Lys Asn Phe
                325                 330